US011478481B2

(12) United States Patent
Raman et al.

(10) Patent No.: US 11,478,481 B2
(45) Date of Patent: *Oct. 25, 2022

(54) PROCESS FOR PREPARATION OF OPTICALLY PURE AND OPTIONALLY SUBSTITUTED 2-(1-HYDROXY-ALKYL)-CHROMEN-4-ONE DERIVATIVES AND THEIR USE IN PREPARING PHARMACEUTICALS

(71) Applicant: Rhizen Pharmaceuticals SA, La Chaux-de-Fonds (CH)

(72) Inventors: Jayaraman V. Raman, Vadodara (IN); Swaroop K. Vakkalanka, La Chaux-de-Fonds (CH)

(73) Assignee: RHIZEN PHARMACEUTICALS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/156,378

(22) Filed: Oct. 10, 2018

(65) Prior Publication Data

US 2019/0038634 A1    Feb. 7, 2019

Related U.S. Application Data

(60) Division of application No. 15/073,324, filed on Mar. 17, 2016, now Pat. No. 10,130,635, which is a continuation of application No. 14/398,902, filed as application No. PCT/IB2013/053544 on May 3, 2013, now Pat. No. 9,309,216.

(60) Provisional application No. 61/671,956, filed on Jul. 16, 2012.

(30) Foreign Application Priority Data

May 4, 2012 (IN) .......................... 1737/CHE/2012

(51) Int. Cl.
| *A61K 31/352* | (2006.01) |
| *C07D 311/36* | (2006.01) |
| *A61K 31/5377* | (2006.01) |
| *A61K 31/52* | (2006.01) |
| *C07D 487/04* | (2006.01) |
| *C07D 311/58* | (2006.01) |
| *C07D 487/14* | (2006.01) |
| *C07D 473/34* | (2006.01) |
| *C07B 55/00* | (2006.01) |

(52) U.S. Cl.
CPC ........ *A61K 31/5377* (2013.01); *A61K 31/352* (2013.01); *A61K 31/52* (2013.01); *C07B 55/00* (2013.01); *C07D 311/36* (2013.01); *C07D 311/58* (2013.01); *C07D 473/34* (2013.01); *C07D 487/04* (2013.01); *C07D 487/14* (2013.01); *C07B 2200/07* (2013.01)

(58) Field of Classification Search
CPC .. A61K 31/5377; A61K 31/52; A61K 31/352; C07B 55/00; C07B 2200/07; C07D 487/04; C07D 311/36; C07D 473/34; C07D 487/14; C07D 311/58
See application file for complete search history.

(56) References Cited

U.S. PATENT DOCUMENTS

| 4,841,077 A | 6/1989 | Ito et al. |
| 7,652,020 B2 | 1/2010 | Guo et al. |
| 9,150,579 B2 | 10/2015 | Vakkalanka et al. |

FOREIGN PATENT DOCUMENTS

| CN | 101027295 A | 8/2007 | |
| EP | 0245518 A1 | 11/1987 | |
| WO | WO-2011055215 A2 * | 5/2011 | ........... C07D 311/36 |
| WO | WO-2012151525 A1 | 11/2012 | |
| WO | WO-2013164801 A1 | 11/2013 | |

OTHER PUBLICATIONS

Conversion of Alcohols To Alkyl Halides With SOCL2 and PBR3 (Year: 2019).*
International Search Report issued in PCT/IB2013/053544 dated Sep. 16, 2013.
Daia, et al., The Directed Lithiation of Some 3-Acylchromone Acetals, Tetrahedron Letters, 1998, 39:1215-1218.
Daia, et al., Synthesis and cycloadditions of 9-H-furo[3,4-b][1]benzo(thio)pyran-9-ones: furan ring formation by a novel hydrolytically induced cycloreversion, Tetrahedron Letters, 2002, 43:4507-4510.

* cited by examiner

*Primary Examiner* — Kortney L. Klinkel
*Assistant Examiner* — Jason Deck
(74) *Attorney, Agent, or Firm* — Blank Rome LLP

(57) ABSTRACT

The present invention relates to compounds useful as pharmaceutical intermediates, to processes for preparing the intermediates, to intermediates used in the processes, and to the use of the intermediates in the preparation of pharmaceuticals. In particular, the present invention concerns enantiomerically pure optionally substituted 2-(1-hydroxy-alkyl)-chromen-4-one derivatives represented by formula (IA) and (IB), processes for preparing the alcohol derivatives and their use in preparing pharmaceuticals.

5 Claims, No Drawings

PROCESS FOR PREPARATION OF OPTICALLY PURE AND OPTIONALLY SUBSTITUTED 2-(1-HYDROXY-ALKYL)-CHROMEN-4-ONE DERIVATIVES AND THEIR USE IN PREPARING PHARMACEUTICALS

PRIORITY

This application is a divisional of U.S. patent application Ser. No. 15/073,324, filed Mar. 17, 2016, which is a continuation of U.S. Ser. No. 14/398,902, filed Nov. 4, 2014, which is the U.S. national phase of International Application No. PCT/IB2013/053544, filed May 3, 2013, which claims the benefit of Indian Provisional Patent Application No. 1737/CHE/2012, filed May 4, 2012, and U.S. Provisional Application No. 61/671,956, filed Jul. 16, 2012, each of which is hereby incorporated by reference.

FIELD OF THE INVENTION

The present invention relates to compounds useful as pharmaceutical intermediates, to processes for preparing the intermediates, to intermediates used in the processes, and to the use of the intermediates in the preparation of pharmaceuticals. In particular, the present invention concerns enantiomerically pure optionally substituted 2-(1-hydroxy-alkyl)-chromen-4-one derivatives, processes for preparing the alcohol derivatives and their use in preparing pharmaceuticals.

BACKGROUND OF THE INVENTION

International Publication No. WO 2011/055215, International Publication No. WO2012151525A1, U.S. Publication No. 2011/0118257, U.S. Publication No. 2012/0289496, Indian Provisional Patent Application Nos. 1542/CHE/2011 dated 4 May 2011 and 81/CHE/2012 dated 9 Jan. 2012 (all of which are incorporated herein by reference in their entirety for all purposes) generally disclose 2,3 disubstituted-4H-chromen-4-one compounds as PI3K inhibitors useful for the treatment, prevention and/or amelioration of kinase mediated diseases or disorders.

SUMMARY OF THE INVENTION

The present inventors have developed an improved process for preparing optionally substituted 2-(1-hydroxy-alkyl)-chromen-4-one derivatives (including 2-(1-hydroxyalkyl), 6-substituted 4H-chromen-4-one compounds), which may be used in the preparation of 2,3 disubstituted-4H-chromen-4-one compounds. The process is particularly useful for preparing enantiomerically pure optionally substituted 2-(1-hydroxy-alkyl)-chromen-4-one derivatives. The process is enantioselective and suitable for large scale production, has high yield, uses non-hazardous reagents and results in less waste.

The present invention provides processes for preparing a compound of formula (IA)

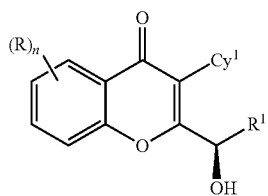

IA wherein
each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^x$R$^y$, —N(R$^x$)SOR$^x$, —N(R$^x$)SO$_2$R$^y$, —NR$^x$C(O)OR$^y$, —NR$^x$C(O)R$^y$, —NR$^x$C(S)R$^y$, —NR$^x$C(S)NR$^x$R$^y$, —SONR$^x$R$^y$, —SO$_2$NR$^x$R$^y$, —OR$^x$, —OR$^x$C(O)NR$^x$R$^y$, —OR$^x$C(O)OR$^x$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO$_2$R$^x$, and —ONO$_2$, wherein each occurrence of R$^x$, R$^y$ and R$^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of R$^x$ and R$^y$, when bound to a common atom, are joined to form a substituted or unsubstituted, saturated or unsaturated 3-14 membered ring, which may optionally include heteroatoms which may be the same or different and are selected from O, NR$^z$ or S, or (ii) any two of R$^x$ and R$^y$, when bound to a common atom, are joined to form an oxo (=O), thio (=S) or imino (=NR$^f$) (wherein R$^f$ is hydrogen or substituted or unsubstituted alkyl);

R$^1$ is substituted or unsubstituted C$_{1-6}$ alkyl;

Cy$^1$ is a group (e.g., a monocyclic or bicyclic group) selected from substituted or unsubstituted cycloalkyl, substituted or unsubstituted heterocyclic group, substituted or unsubstituted aryl and substituted or unsubstituted heteroaryl; and n is an integer selected from 0, 1, 2, 3 or 4.

In one embodiment, the compound is not selected from

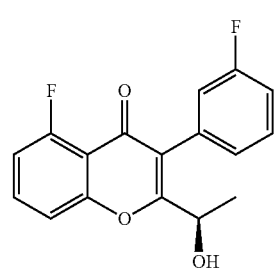 [SMILES: C[C@@H](O)c1oc2cccc(F)c2c(=O)c1-c1cccc(F)c1]

or a salt thereof.

Further preferred is a compound of formula (IA) wherein R is alkyl (e.g., C$_1$-C$_4$ alkyl, such as methyl or ethyl) or halogen.

Further preferred is a compound of formula (IA) wherein R is chloro, fluoro or methyl.

Further preferred is a compound of formula (IA) wherein Cy¹ is a monocyclic group selected from substituted or unsubstituted aryl.

Further preferred is a compound of formula (IA) wherein Cy¹ is selected from

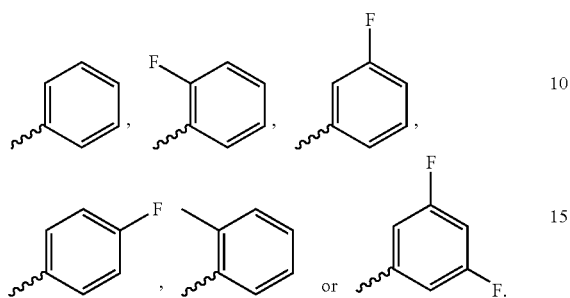

Further preferred is a compound of formula (IA) wherein $R^1$ is methyl or ethyl.

Further preferred is a compound of formula (IA) wherein n is 1.

In yet another embodiment is a compound selected from
1. (R)-6-fluoro-3-(3-fluorophenyl)-2-(1-hydroxyethyl)-4H-chromen-4-one
2. (R)-2-(1-hydroxyethyl)-5-methyl-3-phenyl-4H-chromen-4-one
3. (R)-6-fluoro-2-(1-hydroxyethyl)-3-phenyl-4H-chromen-4-one
4. (R)-2-(1-hydroxyethyl)-3-phenyl-4H-chromen-4-one
5. (R)-3-(3-fluorophenyl)-2-(1-hydroxypropyl)-4H-chromen-4-one
6. (R)-3-(3-fluorophenyl)-2-(1-hydroxyethyl)-4H-chromen-4-one
7. (S)-3-(3-fluorophenyl)-2-(1-hydroxyethyl)-4H-chromen-4-one;

TABLE 1

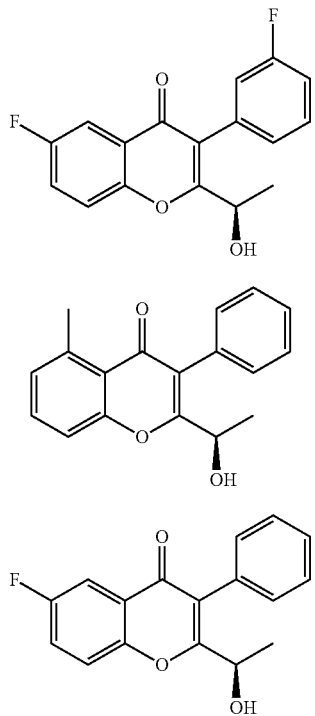

Example-1

Example-2

Example-3

TABLE 1-continued

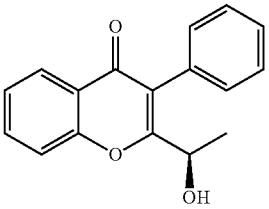 [SMILES: C[C@@H](O)c1oc2ccccc2c(=O)c1-c1ccccc1]

Example-4

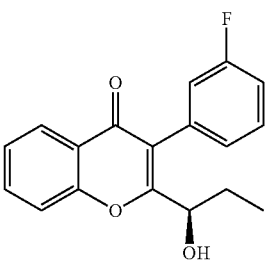 [SMILES: CC[C@@H](O)c1oc2ccccc2c(=O)c1-c1cccc(F)c1]

Example-5

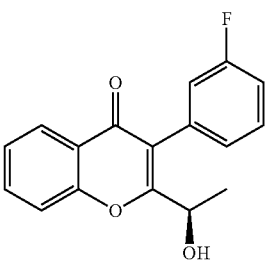 [SMILES: C[C@@H](O)c1oc2ccccc2c(=O)c1-c1cccc(F)c1]

Example-6

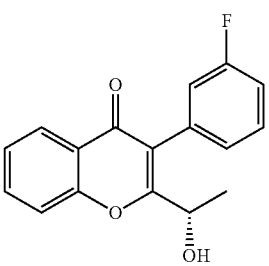 [SMILES: C[C@H](O)c1oc2ccccc2c(=O)c1-c1cccc(F)c1]

Example-7

One embodiment is a process of preparing a compound of formula (IA) which includes (a) treating a compound of formula (6) wherein R, n and Cy¹ are as defined above with a compound of formula (A) wherein $R^1$ is as defined above and Pg is a protecting group (such as benzyl)

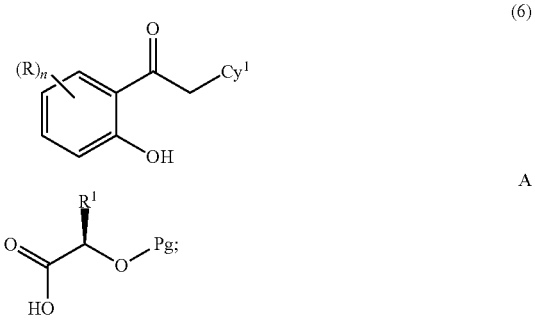

and
(b) deprotecting the compound formed in step (a) to obtain a compound of formula (IA), and optionally converting it to its salt.

In yet another embodiment, the reaction of compound of formula (6) with compound of formula A is performed in presence of a suitable coupling reagent such as HATU ((2-(7-Aza-1H-benztriazole-1-yl)-1,1,3,3-tetramethyluronium hexafluorophosphate), HBTU (O-Benzotriazole-N,N,N',N'-tetramethyl-uronium-hexafluoro-phosphate), TBTU (O-(Benzotriazol-1-yl)-N,N,N',N'-tetramethyl uronium tetrafluoroborate), COMU (Morpholinium, 4-[[[(1-cyano-2-ethoxy-2-oxoethylidene)amino] oxayl] (dimethyl amino) methylene]-hexafluorophosphate), TOTU ((O-[(Ethoxy carbonyl) cyanomethylenamino]-N,N,N',N'-tetra methyl uronium tetrafluoroborate), HCTU ((2-(6-Chloro-1H-benzotriazole-1-yl)-1,1,3,3-tetramethylaminium hexafluorophosphate), TCTU (O-(6-Chloro-1-hydrocibenzotriazol-1-yl)-1,1,3,3-tetramethyl uronium tetra fluoroborate), TATU (O-(7-Azabenzotriazole-1-yl)-N,N,N',N'-tetramethyl uronium tetra fluoroborate), TSTU (O—(N-Succinimidyl)-1,1,3,3-tetramethyl uranium tetrafluoroborate), TDBTU (N,N,N',N'-Tetramethyl-O-(3,4-dihydro-4-oxo-1,2,3-benzotriazin-3-yl) uranium tetrafluoroborate), any other suitable coupling reagents, or any combination of any of the foregoing.

Further preferred is where the reaction of compound of formula (6) with compound of formula A is performed in presence of HATU, HBTU, TBTU or COMU.

Further preferred is where the reaction of compound of formula (6) with compound of formula A is performed in presence of HATU.

Another embodiment is a process for preparing a compound of formula (IB)

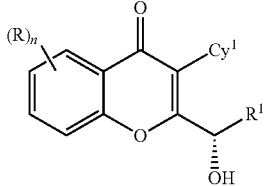
IB wherein all the variables are as defined above, the method includes the steps of
(a) treating a compound of formula (6), wherein R, n and Cy¹ are as defined above, with a compound of formula (B) wherein R¹ is as defined above and Pg is a protecting group (such as benzyl)

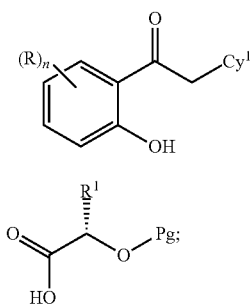
(6)

B and
(b) deprotecting the compound formed in step (a) to obtain a compound of Formula (IB).

In one embodiment, the compound is not selected from

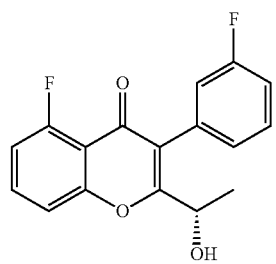 [SMILES: C[C@H](O)c1oc2cccc(F)c2c(=O)c1-c1cccc(F)c1]

or a salt thereof.

Further preferred is a compound of formula (IB) wherein R is alkyl (e.g., $C_1$-$C_4$ alkyl, such as methyl or ethyl) or halogen.

Further preferred is a compound of formula (IB) wherein R is chloro, fluoro or methyl.

Further preferred is a compound of formula (IB) wherein Cy¹ is a monocyclic group selected from substituted or unsubstituted aryl.

Further preferred is a compound of formula (IB) wherein Cy¹ is selected from

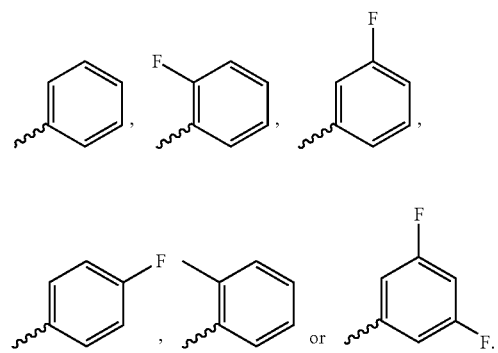

Further preferred is a compound of formula (IB) wherein R¹ is methyl or ethyl.

Further preferred is a compound of formula (IB) wherein n is 1.

Yet another embodiment is a process for preparing a compound of formula (IA)

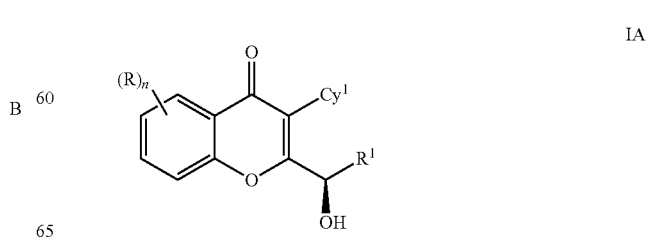
IA wherein all the variables are as defined above, the method includes the steps of (a) converting a compound of formula (1)

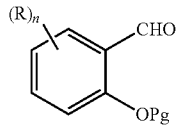
1 wherein R and n are as defined above and Pg is a protecting group, to a compound of formula (2)

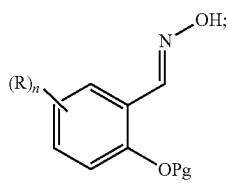
2

(b) converting the compound of formula (2) to a compound of formula (3)

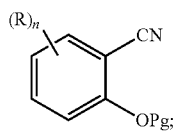
3

(c) converting the compound of formula (3) to a compound of formula (5)

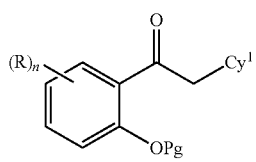
5 wherein R, n, $Cy^1$ and Pg are as described above;

(d) deprotection of the compound of formula (5) to give a compound of formula (6)

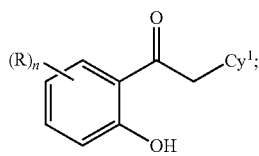
6

(e) reacting the compound of formula (6) with a compound of formula (A)

A to give a compound of formula (7a)

7a (f) deprotection of the compound of formula (7a) to give the desired compound of formula (IA); and
(g) optionally, converting the compound of formula (IA) to a salt of the compound.

The compound of Formula (1) may be converted to a compound of Formula (2) by treating the compound of formula (1) with hydroxyl amine or a salt thereof (such as $NH_2OH.HCl$) in presence of a base. The compound of Formula (3) may be obtained by treating the compound of formula (2) with N,N'-carbonyldiimidazole (CDI). The compound of Formula (3) may be converted to a compound of Formula (5) by treating the compound of formula (3) with a Grignard reagent of formula (4a)

$Cy^1$-$CH_2$—MgX wherein X is halogen and $Cy^1$ is as defined above.

Yet another embodiment is a process for preparing a compound of formula (IB)

1B wherein all the variables are as defined above, the process includes the steps of (a) converting a compound of formula (1)

1 to a compound of formula (2)

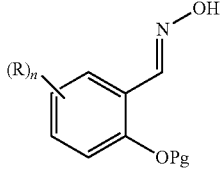

wherein R and n are as defined above and Pg is a protecting group (for example by reacting the compound of formula (1) with hydroxylamine or a salt thereof (such as NH₂OH.HCl) in presence of a base);

(b) converting the compound of formula (2) to a compound of formula (3)

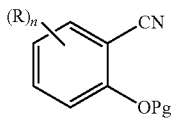

(for example, by treating the compound of formula (2) with N,N'-carbonyldiimidazole (CDI)):

(c) converting the compound of formula (3) to a compound of formula (5)

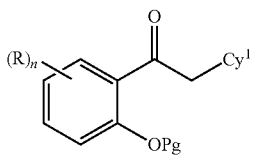

wherein R, n, $Cy^1$ and Pg are as described above (for example by treating the compound of formula (3) with a Grignard reagent of formula (4a)

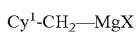

wherein X is halogen and $Cy^1$ is as defined above);

(d) deprotection of the compound of formula (5) to give a compound of formula (6)

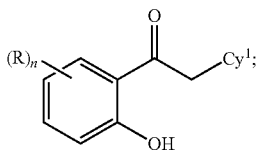

(e) reacting the compound of formula (6) with a compound of formula (B)

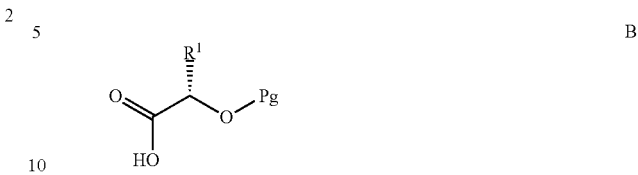

to give a compound of formula (7b)

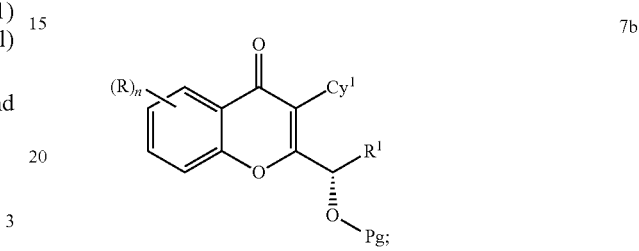

(f) deprotection of the compound of formula (7b) to give the desired compound of formula (IB) wherein all the variables (R, $R^1$, n and $Cy^1$) are as described above in relation to Formula (IA); and (g) optionally, converting the compound of formula (IB) to a salt of the compound.

In yet another embodiment, the reaction of compound of formula (6) with compound of formula B is performed in presence of a suitable coupling reagent such as HATU ((2-(7-Aza-1H-benzotriazole-1-yl)-1,1,3,3-tetramethyluronium hexafluorophosphate), HBTU (O-Benzotriazole-N,N,N',N'-tetramethyl-uronium-hexafluoro-phosphate), TBTU (O-(Benzotriazol-1-yl)-N,N,N',N'-tetramethyl uronium tetrafluoroborate), COMU (Morpholinium, 4-[[[(1-cyano-2-ethoxy-2-oxoethylidene)amino] oxayl] (dimethyl amino) methylene]-hexafluorophosphate), TOTU ((O-[(Ethoxy carbonyl) cyanomethylenamino]-N,N,N',N'-tetra methyl uronium tetrafluoroborate, HCTU ((2-t 6-Chloro-1H-benzotriazole-1-yl)-1,1,3,3-tetramethylaminium hexafluorophosphate), TCTU (O-(6-Chloro-1-hydrocibenzotriazol-1-yl)-1,1,3,3-tetramethyl uronium tetra fluoroborate), TATU (O-(7-Azabenzotriazole-1-yl)-N,N,N',N'-tetramethyl uronium tetra fluoro orate), TSTU (O—(N—Succinimidyl-1,1,3,3-tetramethyl uranium tetrafluoroborate), TDBTU (N,N,N',N'-Tetramethyl-O-(3,4-dihydro-4-oxo-1,2,3-benzotriazin-3-yl) uranium tetrafluoroborate), any other suitable coupling reagents, or any combination of any of the foregoing.

Further preferred is where the reaction of compound of formula (6) with compound of formula B is performed in presence of HATU, HBTU, TBTU or COMU.

Further preferred is where the reaction of compound of formula (6) with compound of formula B is performed in presence of HATU.

Yet another embodiment is a process for inverting a compound of formula (IA) to yield a compound of formula (IB) comprising the step of (a) reacting the compound of formula (IA) with R'—COOH (wherein $R^1$ is selected from substituted or unsubstituted alkyl or substituted or unsubstituted aryl) to provide a compound of formula IA-2

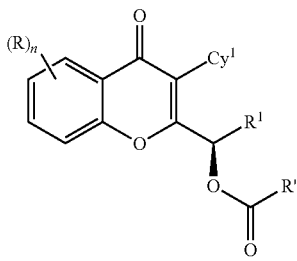

IA-2

(b) treating the compound of formula (IA-2) with a suitable base in a polar solvent to yield a compound of formula (IB).

Yet another embodiment is a process for inverting a compound of formula (IB) to yield a compound of formula (IA) comprising the step of
(a) reacting the compound of formula (IB) with R'—COOH (wherein R' is selected from substituted or unsubstituted alkyl or substituted or unsubstituted aryl) to provide a compound of formula IB-2

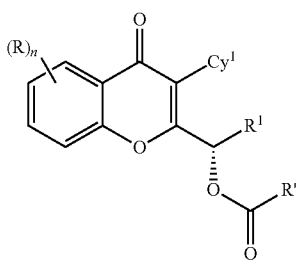

IB-2

(b) treating the compound of formula (IB-2) with a suitable base in a polar solvent to yield a compound of formula (IA).

Further preferred is where R' is 4-chloro phenyl.

Further preferred is where the base is selected from inorganic bases, such as $K_2CO_3$, $Na_2CO_3$ or $CsCO_3$ and the polar solvent used is a suitable alcohol selected from methanol or ethanol.

Yet another embodiment is a process for preparing a compound of formula (IA-I)

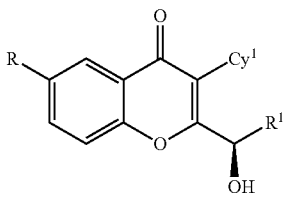

IA-I wherein all the variables are as defined above, the method comprising the steps of
(a) converting a compound of formula (1a)

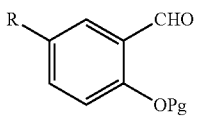

1a to a compound of formula (2a)

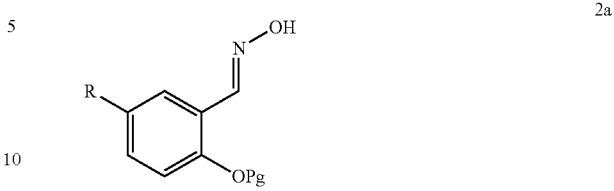

2a wherein R and n are as defined above and Pg is a protecting group (for example, reacting a compound of formula (1a) with hydroxylamine or a salt thereof (such as $NH_2OH.HCl$) in the presence of a base);

(b) converting a compound of formula (2a) to a compound of formula (3a)

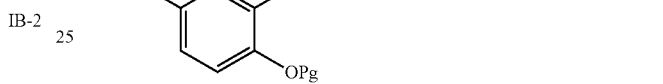

3a (for example, by treating the compound of formula (2a) with N,N'-carbonyldiimidazole (CDI));

(c) converting a compound of formula (3a) to a compound of formula (5a)

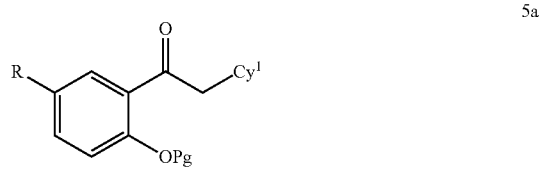

5a (for example, by treating the compound of formula (3a) with a Grignard reagent of formula (4a)

Cy¹-CH₂—MgX    4a wherein X is halogen and $Cy^1$ is as described above);

(d) deprotection of the compound of formula (5a) to give a compound of formula (6a)

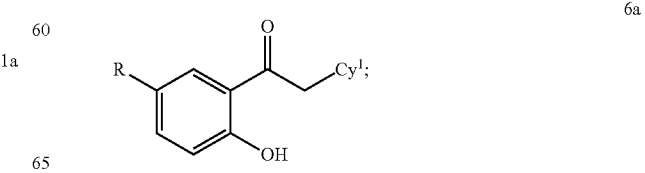

6a (e) reacting the compound of formula (6a) with a compound of formula (A)

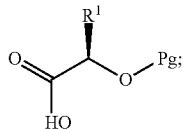

to give a compound of formula (7aa)

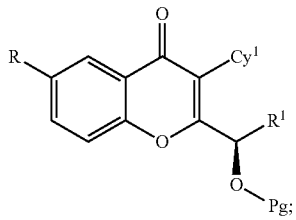

(f) deprotection of the compound of formula (7aa) to give the desired compound of formula (IA-1) wherein all the variables (R, $R^1$, n and $Cy^1$) are as described above in relation to Formula (IA); and (g) optionally, converting the compound of formula (IA-1) to a salt of the compound.

Yet another embodiment is a process for preparing a compound of formula (IA-II)

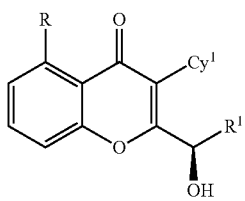

wherein all the variables are as defined above, the methods comprising the step of (a) converting a compound of formula (1b)

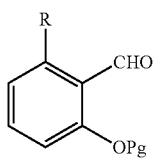

wherein R is as defined above and Pg is a protecting group, to a compound of formula (2b)

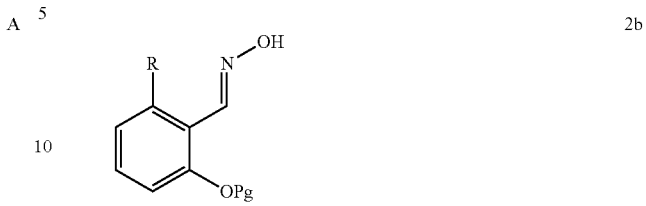

(for example, by treating a compound of formula (1a) with hydroxylamine or a salt thereof (such as $NH_2OH \cdot HCl$) in the presence of a base);

(b) converting a compound of formula (2b) to a compound of formula (3b)

(for example, by treating the compound of formula (2b) with N,N'-carbonyldiimidazole (CDI));

(c) converting the compound of formula (3b) to a compound of formula (5b)

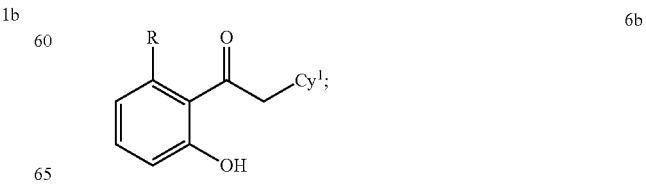

(for example, treating a compound of formula (3b) with a Grignard reagent of formula (4a)

$$Cy^1\text{-}CH_2\text{---}MgX \qquad 4a$$

wherein X is halogen and $Cy^1$ is as described above);

(d) deprotection of the compound of formula (5b) to give a compound of formula (6b)

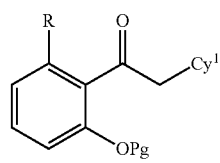

(e) reacting the compound of formula (6b) with a compound of formula (A)

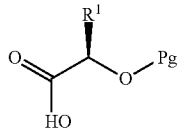

to give a compound of formula (7ab)

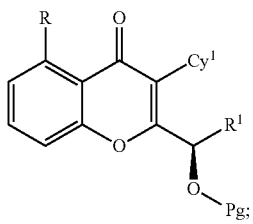

and (f) deprotection of the compound of formula (7ab) to give the desired compound of formula (IA-II) wherein all the variables (R, $R^1$, n and $Cy^1$) are as described above in relation to Formula (IA); and (g) optionally, converting the compound of formula (IA-II) to a salt of the compound.

Yet another embodiment is a process for inverting a compound of formula (IA-I) to yield a compound of formula (IB-I) (shown below) comprising the step of (a) reacting the compound of formula (IA-I) with R'—COOH (wherein R' is selected from substituted or unsubstituted alkyl or substituted or unsubstituted aryl) to provide a compound of formula (IA-I2)

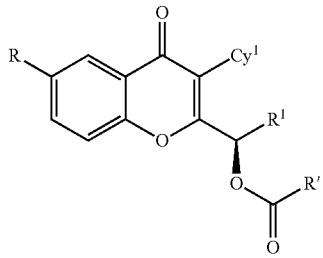

(b) treating the compound of formula (IA-I2) with a suitable base in a polar solvent to yield a compound of formula (IB-I).

Yet another embodiment is a process for inverting a compound of formula (IB-I) to yield a compound of formula (IA-I) comprising the step of (a) reacting the compound of formula (IB-I) with R'—COOH (wherein R' is selected from substituted or unsubstituted alkyl or substituted or unsubstituted aryl) to provide a compound of formula (IB-I2)

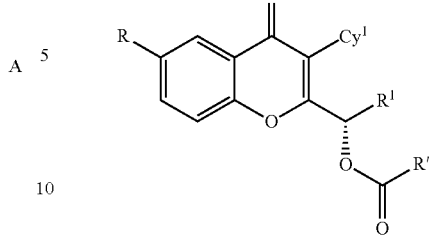

(b) treating the compound of formula (IB-I2) with a suitable base in a polar solvent to yield a compound of formula (IA-I).

Yet another embodiment is a process for preparing a compound of formula (IB-I)

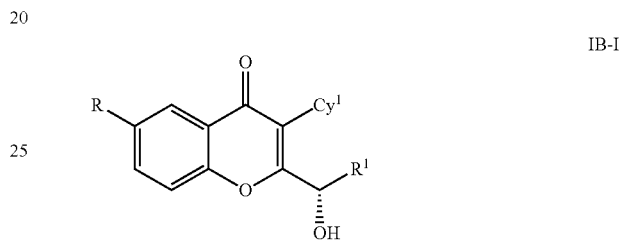

wherein all the variables are as defined above, the method comprising the steps of (a) reacting the compound of formula (6a) with a compound of formula (B)

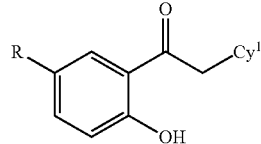

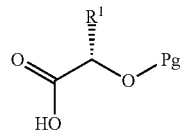

to give a compound of formula (7ba)

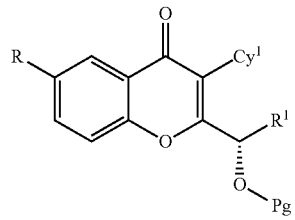

(b) deprotection of the compound of formula (7ba) to give the desired compound of formula (IB-I) wherein all the variables (R, $R^1$, n and $Cy^1$) are as described above in relation to Formula (IA); and (c) optionally, converting the compound of formula (IB-I) to a salt of the compound.

Yet another embodiment is a process for preparing a compound of formula (IB-II)

IB-II wherein all the variables are as defined above, the method comprising the steps of (a) reacting the compound of formula (6b) with a compound of formula (B)

6b

B to give a compound of formula (7bb)

7bb (b) deprotection of the compound of formula (7bb) to give the desired compound of formula (IB-II) wherein all the variables (R, R¹, n and Cy¹) are as described above in relation to Formula (IA); and (c) optionally, converting the compound of formula (IB-II) to a salt of the compound.

Yet another embodiment is a process for inverting a compound of formula (IA-II) to yield a compound of formula (IB-II) comprising the step of (a) reacting the compound of formula (IA-II) with R'—COOH (wherein R' is selected from substituted or unsubstituted alkyl or substituted or unsubstituted aryl) to provide a compound of formula IA-II2

IA-II2

(b) treating the compound of formula (IA-II2) with a suitable base in a polar solvent to yield a compound of formula (IB-II).

Yet another embodiment is a process for inverting a compound of formula (IB-II) to yield a compound of formula (IA-II) comprising the step of (a) reacting the compound of formula (IB-II) with R'—COOH (wherein R' is selected from substituted or unsubstituted alkyl or substituted or unsubstituted aryl) to provide a compound of formula IB-II2

IB-II2

(b) treating the compound of formula (IB-II2) with a suitable base in a polar solvent to yield a compound of formula (IA-II).

Yet another embodiment is a compound of formula (IA) or (IB)

IA

IB or a salt thereof, wherein the variables R, n, Cy¹, and R¹ are defined as above.

In one embodiment, the compound of formula (IA) or (IB) has an enantiomeric excess (EE) of at least 75%, 90%, 95%, 97%, or 98%.

Yet another embodiment is the use of the compound of formula (IA), or any other intermediate described herein, for preparation of PI3K inhibitors of formula (I)

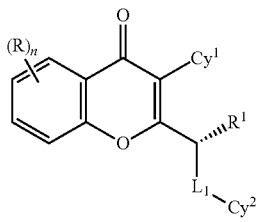

(I)

or a tautomer thereof, N-oxide thereof, pharmaceutically acceptable ester thereof, prodrug thereof, or pharmaceutically acceptable salt thereof, wherein
the variables R, n, $Cy^1$, and $R^1$ are defined as above:
$Cy^2$ is selected from a substituted or unsubstituted heterocyclic group, substituted or unsubstituted aryl and substituted or unsubstituted heteroaryl;
$L_1$ is absent or selected from $—(CR^aR^b)_q—$, $—O—$, $—S(\!=\!O)_q—$, $—NR'—$ or $—C(\!=\!Y)—$;
each occurrence of $R^a$ and $R^b$ may be the same or different and are independently selected from hydrogen, halogen, hydroxy, cyano, substituted or unsubstituted $(C_{1-6})$alkyl, $—NR^cR^d$ (wherein $R^c$ and $R^d$ are independently hydrogen, halogen, hydroxy, cyano, substituted or unsubstituted $(C_{1-6})$alkyl, or $(C_{1-6})$alkoxy) and $—OR^c$ (wherein $R^c$ is substituted or unsubstituted $(C_{1-6})$alkyl) or when $R^a$ and $R^b$ are directly bound to a common atom, they may be joined to form an oxo group (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, $NR^d$ (wherein $R^d$ is hydrogen or substituted or unsubstituted $(C_{1-6})$alkyl) or S;
Y is selected from O, S, and $NR^a$; and
q is 0, 1 or 2.

The compound of formula (1) may be prepared by
(a) treating the compound of formula (IA)

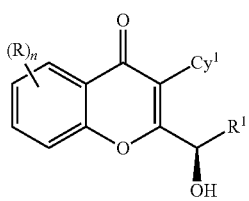

IA with $Cy^2$-H (for example, by a Mitsunobu reaction) to give the desired compound of formula (I) or a tautomer thereof, N-oxide thereof, pharmaceutically acceptable ester thereof, prodrug thereof, or pharmaceutically acceptable salt thereof, wherein
R, $R^1$, n and $Cy^1$ are as described above in relation to Formula (IA).
$Cy^2$ is selected from a substituted or unsubstituted heterocyclic group, substituted or unsubstituted aryl and substituted or unsubstituted heteroaryl; and $L_1$ is absent; and
(b) optionally converting the compound of formula (I) to a salt of the compound.

The compound of formula (I) may also be prepared by
(a) treating the compound of formula (IA)

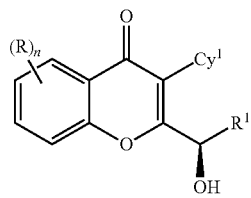

IA with a phosphorus halide or mesyl chloride (or other mesyl halide) in the presence of a base to give a compound of formula (8a)

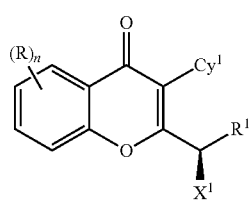

8a wherein $X^1$ is halogen or —O-Mesyl (i.e., $—O—SO_2CH_3$); and
(b) reacting the compound of formula (8a) with $Cy^2$-H in the presence of a base to give the desired compound of formula (I) or a tautomer thereof, N-oxide thereof, pharmaceutically acceptable ester thereof, prodrug thereof, wherein
R, $R^1$, n and $Cy^1$ are as described above in relation to Formula (IA);
$Cy^2$ is selected from a substituted or unsubstituted heterocyclic group, substituted or unsubstituted aryl and substituted or unsubstituted heteroaryl; and
$L_1$ is absent; and
(c) optionally, converting the compound of formula (I) to a salt of the compound.

Yet another embodiment provided is the use of the compound of formula (IA) for preparation of PI3K inhibitors of formula (II)

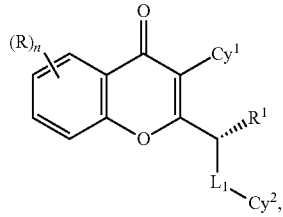

(II)

or a tautomer thereof, N-oxide thereof, pharmaceutically acceptable ester thereof, prodrug thereof, wherein
R, $R^1$, n and $Cy^1$ are as described above in relation to Formula (IA);
$Cy^2$ is selected from a substituted or unsubstituted heterocyclic group, substituted or unsubstituted aryl and substituted or unsubstituted heteroaryl; and
$L_1$ is NH.

The compound of formula (II) may be prepared by
(a) treating the compound of formula (IA)

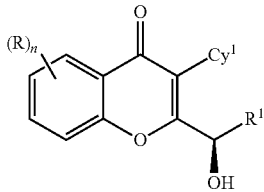

IA with a phosphorus halide or mesyl chloride (or other mesyl halide) in the presence of a base to give a compound of formula (8a)

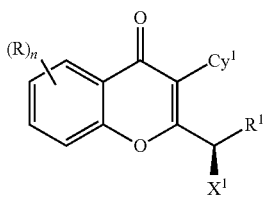

8a wherein $X^1$ is halogen or —O-Mesyl;
(b) converting the compound of formula (8a) to give a compound of formula (9a)

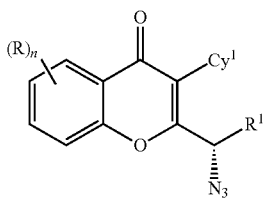

9a (for example, by treating the compound of formula (8a) with sodium azide);
(c) converting the compound of formula (9a) to give a compound of formula (10a)

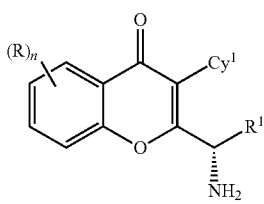

10a (for example, by treating the compound of formula (8a) with triphenyl phosphine);
(d) coupling the compound of formula (10a) with a compound of formula $Cy^2$-Lg, wherein Lg is a leaving group, in the presence of a base to give the desired compound of formula (II); and
(e) optionally, converting the compound of formula (II) to a salt of the compound.

Yet another embodiment is the use of the compound of formula (IB), or any other intermediate described herein, for preparation of PI3K inhibitors of formula (III)

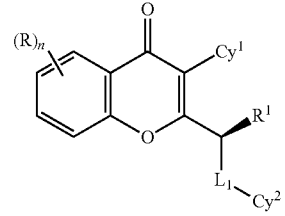

(III)

or a tautomer thereof, N-oxide thereof, pharmaceutically acceptable ester thereof, prodrug thereof, or pharmaceutically acceptable salt thereof, wherein
the variables R, n, $Cy^1$, and $R^1$ are defined as above;
$Cy^2$ is selected from a substituted or unsubstituted heterocyclic group, substituted or unsubstituted aryl and substituted or unsubstituted heteroaryl;
$L_1$ is absent or selected from —$(CR^aR^b)_q$—, —O—, —S(=O)$_q$—, —NR$^a$— or —C(=Y)—;
each occurrence of $R^a$ and $R^b$ may be the same or different and are independently selected from hydrogen, halogen, hydroxy, cyano, substituted or unsubstituted $(C_{1-6})$alkyl, —NR$^c$R$^d$ (wherein R$^c$ and R$^d$ are independently hydrogen, halogen, hydroxy, cyano, substituted or unsubstituted $(C_{1-6})$alkyl, or $(C_{1-6})$alkoxy) and —OR$^c$ (wherein R$^c$ is substituted or unsubstituted $(C_{1-6})$alkyl) or when R$^a$ and R$^b$ are directly bound to a common atom, they may be joined to form an oxo group (=O) or form a substituted or unsubstituted, saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted $(C_{1-6})$alkyl) or S;
Y is selected from O, S, and NR$^a$; and
q is 0, 1 or 2.

The compound of formula (III) may be prepared by
(a) treating the compound of formula (IB)

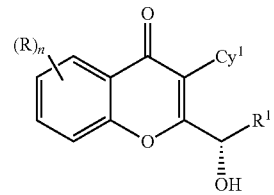

IB with $Cy^2$-H (for example, by a Mitsunobu reaction) to give the desired compound of formula (III) or a tautomer thereof, N-oxide thereof, pharmaceutically acceptable ester thereof, prodrug thereof, or pharmaceutically acceptable salt thereof, wherein
R, $R^1$, n and $Cy^1$ are as described above in relation to Formula (IB);
$Cy^2$ is selected from a substituted or unsubstituted heterocyclic group, substituted or unsubstituted aryl and substituted or unsubstituted heteroaryl; and L₁ is absent; and
(b) optionally converting the compound of formula (III) to a salt of the compound.

The compound of formula (III) may also be prepared by
(a) treating the compound of formula (IB)

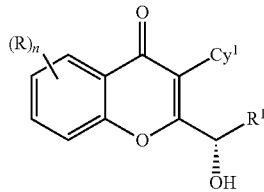

IB with a phosphorus halide or mesyl chloride (or other mesyl halide) in the presence of a base to give a compound of formula (8b)

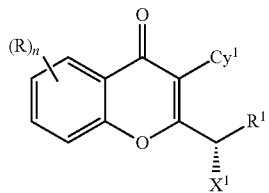

8b wherein X¹ is halogen or —O-Mesyl (i.e., —O—SO₂CH₃); and
(b) reacting the compound of formula (8b) with Cy²-H in the presence of a base to give the desired compound of formula (III) or a tautomer thereof, N-oxide thereof, pharmaceutically acceptable ester thereof, prodrug thereof, or pharmaceutically acceptable salt thereof, wherein R, R¹, n and Cy¹ are as described above in relation to Formula (IB);

Cy² is selected from a substituted or unsubstituted heterocyclic group, substituted or unsubstituted aryl and substituted or unsubstituted heteroaryl; and L₁ is absent; and (c) optionally, converting the compound of formula (III) to a salt of the compound.

Yet another embodiment provided is the use of the compound of formula (IB) for preparation of PI3K inhibitors of formula (IV)

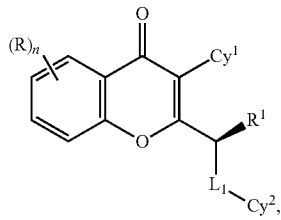

(IV)

or a tautomer thereof, N-oxide thereof, pharmaceutically acceptable ester thereof, prodrug thereof, or pharmaceutically acceptable salt thereof, wherein R, R¹, n and Cy¹ are as described above in relation to Formula (IB);

Cy² is selected from a substituted or unsubstituted heterocyclic group, substituted or unsubstituted aryl and substituted or unsubstituted heteroaryl; and L₁ is NH.

The compound of formula (IV) may be prepared by
(a) treating the compound of formula (IB)

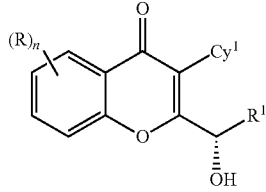

IB with a phosphorus halide or mesyl chloride (or other mesyl halide) in the presence of a base to give a compound of formula (8b)

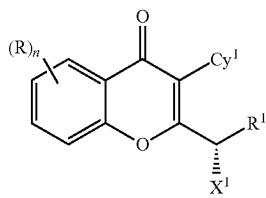

8b wherein X¹ is halogen or —O-Mesyl;
(b) converting the compound of formula (8b) to give a compound of formula (9b)

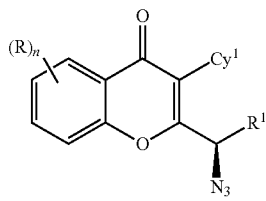

9b (for example, by treating the compound of formula (8b) with sodium azide);
(c) converting the compound of formula (9b) to give a compound of formula (10b)

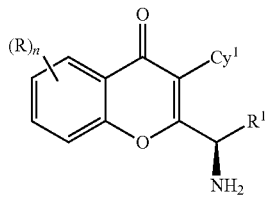

10b (for example, by treating the compound of formula (8b) with triphenyl phosphine);

(d) coupling the compound of formula (10b) with a compound of formula $Cy^2$-Lg, wherein Lg is a leaving group, in the presence of a base to give the desired compound of formula (IV); and (e) optionally, converting the compound of formula (IV) to a salt of the compound.

In one preferred embodiment, the coupling reaction of the compound of formula 6 with the compound of formula A or B is performed in the presence of N-[(Dimethylamino)-1H-1,2,3-triazolo-[4,5-b]pyridin-1-ylmethylene]-N-methyl methanaminium hexafluorophosphate N-oxide (HATU).

The protecting groups, such as those on the compounds of formulas 7a, 7b, 7aa, 7ab, 7ba, and 7bb may be removed using suitable deprotecting agents, such as aluminium chloride, boron tribromide, or any combination of the foregoing. Optionally the deprotection may be performed using other suitable deprotecting agents including use of hydrogenation for deprotection.

Yet another embodiment is a composition (e.g., a pharmaceutical composition) comprising (a) a PI3K inhibitor of formula (I) or (II) or a salt thereof, and (b) a compound of formula (IA) or (IB) or a salt thereof. In one embodiment, the composition comprises at least about 99.5% by weight of the PI3K inhibitor, and the compound of formula (IA) or (IB) in an amount up to 0.5% by weight, based upon the total of components (a) and (b). In another embodiment, the composition includes the compound of formula (IA) or (IB) in an amount up to 0.2% or 0.1% by weight. The pharmaceutical composition can be, for example, a tablet or capsule.

DETAIL DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched or branched chain having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butyl.

The term "alkoxy" denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O-(substituted alkyl) wherein the term "substituted alkyl" is the same as defined above for "alkyl". For example, "alkoxy" refers to the group —O-alkyl, including from 1 to 8 carbon atoms of a straight, branched, cyclic configuration and combinations thereof attached to the parent structure through a oxygen atom. Examples include methoxy, ethoxy, propoxy, isopropoxy, cyclopropyloxy, and cyclohexyloxy.

The term "cycloalkyl" denotes a non-aromatic mono or multicyclic ring system of 3 to about 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl.

The term "cycloalkylalkyl" refers to a cyclic ring-containing radical containing in the range of 3 up to about 8 carbon atoms directly attached to an alkyl group which are then attached to the main structure at any carbon from the alkyl group that results in the creation of a stable structure such as cyclopropylmethyl, cyclobutylethyl, and cyclopentylethyl.

The term "cycloalkenyl" refers to cyclic ring-containing radicals containing in the range of 3 up to about 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure.

The term "aryl" refers to aromatic radicals having in the range of 6 up to 20 carbon atoms such as phenyl, naphthyl, tetrahydronaphthyl, indanyl, and biphenyl.

The term "arylalkyl" refers to an aryl group as defined above directly bonded to an alkyl group as defined above, e.g., —$CH_2CH_5$ and —$C_2H_5C_6H_5$.

The term "heterocyclic ring" refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl" refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide substituents, such as pyridinyl N-oxides.

The term "heteroarylalkyl" refers to a heteroaryl ring radical as defined above directly bonded to an alkyl group. The heteroarylalkyl radical may be attached to the main structure at any carbon atom from alkyl group that results in the creation of a stable structure.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(═N—N(R$^x$)R$^y$), —NR$^x$C(O)OR$^y$, —NR$^x$R$^y$, —NR$^x$C(O)R$^y$, —NR$^x$C(S)R$^y$—NR$^x$C(S)NR$^y$R$^z$, —SONR$^x$R$^y$—, —SO$_2$NR$^x$R$^y$, —OR$^x$, —OR$^x$C(O)NR$^y$R$^z$, —OR$^x$C(O)OR$^y$—, —OC(O)R$^x$, —OC(O)NR$^x$R$^y$, —R$^x$N-R$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^x$ (e.g., R$^x$ can be hydrogen or C$_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups. For example, the terms "fluoroalkyl" and "fluoroalkoxy" include haloalkyl and haloalkoxy groups, respectively, in which the halo is fluorine.

The term "protecting group" or "Pg" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethyloxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH$_2$CH$_2$SO$_2$Ph, cyanoethyl, 2-(trimethylsilyl) ethyl, 2-(trimethylsilyl)ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For instance, the non-limiting example of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups, unless otherwise specified, are halogen atoms and mesyloxy, p-nitrobenzensulphonyloxy and tosyloxy groups.

The term "prodrug" refers to a compound, which is a precursor (for example, an inactive precursor) of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fc, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

Representative processes of the present invention include those specified below. The present invention should not be construed to be limited to them.

EXPERIMENTAL

The examples and preparations provided below further illustrate and exemplify the methods of preparing compounds of the invention. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Example 1

(R)-6-fluoro-3-(3-fluorophenyl)-2-(1-hydroxyethyl)-4H-chromen-4-one

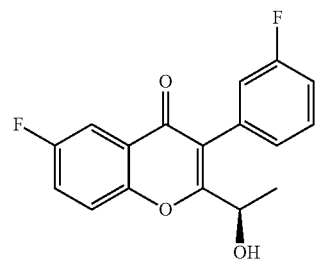 [SMILES: C[C@@H](O)c1oc2ccc(F)cc2c(=O)c1-c1cccc(F)c1]

Step 1: (R)-2-(1-(benzyloxy) ethyl)-6-fluoro-3-(3-fluorophenyl)-4H-chromen-4-one To 1-(5-fluoro-2-hydroxyphenyl)-2-(3-fluorophenyl) ethanone (11 g, 44.31 mmol), in Dichloromethane (110 ml), HATU (33.7 g, 88.63 mmol) and (R)-Benzyloxypropionic acid (9.58 g, 53.17 mmol) were added and stirred for ~10 min. Triethylamine (67 ml, 478 mmol) was added dropwise and stirred at room temperature (RT) for 24 h. The reaction mixture was quenched with water and extracted with Dichloromethane (2×250 ml). The organic layer was dried with sodium sulphate and concentrated under vacuum. The crude product was purified by column chromatography with ethyl acetate:Petroleum ether to afford the title compound as a off-white solid (10.9 g, 63%). $^1$H-NMR (8 ppm, CDCl$_3$, 400 MHz): 7.85 (dd, J=8.1, 3.0 Hz, 1H), 7.58 (dd, J=9.1, 4.1 Hz, 1H), 7.47-7.39 (m, 1H), 7.39-7.34 (m, 1H), 7.28-7.20 (m, 3H), 7.20-7.14 (m, 2H), 7.16-7.14 (m, 1H), 6.99-7.89 (m, 2H), 4.50-4.31 (m, 3H), 1.56 (d, J=6.4 Hz, 3H). Mass: 392.9 (M$^+$).

Step 2: (R)-6-fluoro-3-(3-fluorophenyl)-2-(1-hydroxyethyl)-4H-chromen-4-one

To (R)-2-(1-(benzyloxy)ethyl)-6-fluoro-3-(3-fluorophenyl)-4H-chromen-4-one (10.5 g, 26.69 mmol) in Dichloromethane (110 ml) cooled to 0° C., anhydrous Aluminium chloride (5.35 g, 40.03 mmol) was added portion wise and stirred for 1 h and then at RT for 2 h. The reaction mixture was quenched with dilute aq. HCl (10 ml), extracted with Dichloromethane (2×50 ml). The organic layer was dried over sodium sulphate and concentrated under reduced pressure. The crude product was purified by column chromatography with ethyl acetate:petroleum ether to afford the title compound as off-white solid (6.5 g, 81%). $^1$H-NMR (8 ppm, CDCl$_3$, 400 MHz): 7.86 (dd, J=8.3, 3.0 Hz, 1H), 7.56 (dd, J=9.2, 4.2 Hz, 1H), 7.45 (m, 2H), 7.12-6.99 (m, 3H), 4.76 (q, J=6.6 Hz, 1H), 1.55 (d, J=6.6 Hz, 3H). Mass: 303.2 (M$^+$+1). Purity: 99.78%. $[\alpha]^{25}_D$ 0.287 (c=1, CHCl$_3$). Enantiomeric excess: 97.74%, enriched in the late eluting isomer (retention time: 10.93 min.) as determined by HPLC on a chiralpak AD-H column.

Example 2

(R)-2-(1-hydroxyethyl)-5-methyl-3-phenyl-4H-chromen-4-one

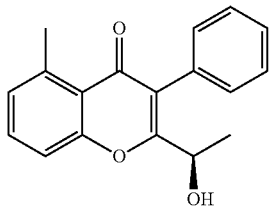 [SMILES: Cc1cccc2oc([C@@H](C)O)c(-c3ccccc3)c(=O)c12]

Step 1: (R)-2-(1-(benzyloxy)ethyl)-5-methyl-3-phenyl-4H-chromen-4-one

To 1-(2-hydroxy-6-methylphenyl)-2-phenylethanone (0.400 g, 1.76 mmol) in dichloromethane (4 ml), R(+)-benzyloxypropionic acid (0.382 g, 2.12 mmol) and HATU (2.01 g, 5.30 mmol) were added followed by triethylamine (2.6 ml, 19.08 mmol). After 20 h at room temperature, the reaction mixture was quenched with water, extracted with ethyl acetate, dried over sodium sulphate and concentrated. The crude product was column chromatographed with ethyl acetate:petroleum ether to afford the title compound as off-white solid (0.080 g, 12%). $^1$H-NMR (6 ppm, CDCl$_3$, 400 MHz): 7.55 (t, J=8.1 Hz, 1H), 7.43-7.13 (m, 12H), 4.47 (m, 2H), 4.30 (d, J=11.8 Hz, 1H), 2.84 (s, 3H), 1.54 (d, J=6.5 Hz, 3H). Mass: 370.9 (M$^+$).

Step 2: (R)-2-(1-hydroxyethyl)-5-methyl-3-phenyl-4H-chromen-4-one

To (R)-2-(1-(benzyloxy)ethyl)-5-methyl-3-phenyl-4H-chromen-4-one (0.850 g, 2.29 mmol) in dichloromethane (8.0 ml) at −78° C., boron tribromide (0.78 ml, IM in dichloromethane, 4.58 mmol) was added slowly and maintained for 4 h. The reaction mass was quenched at −78° C. using 2N HCl (50 ml), extracted with ethyl acetate, dried over sodium sulphate and concentrated. The crude product was column chromatographed with ethyl acetate:petroleum ether to afford the title compound as pale-yellow liquid (0.200 g, 31%). $^1$H-NMR (8 ppm, CDCl$_3$, 400 MHz): 7.54 (t, J=8.0 Hz, 1H), 7.46-7.26 (m, 6H), 7.13 (d, J=7.4 Hz, 1H), 4.71 (q, J=6.6 Hz, 1H), 2.83 (s, 3H), 1.53 (d, J=6.6 Hz, 3H). Mass: 280.8 (M$^+$).

Example 3

(R)-6-fluoro-2-(1-hydroxyethyl)-3-phenyl-4H-chromen-4-one

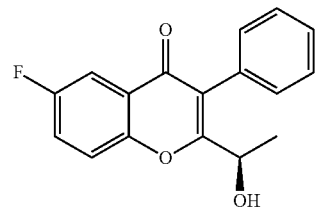 [SMILES: C[C@@H](O)c1oc2ccc(F)cc2c(=O)c1-c1ccccc1]

Step 1: (R)-2-(1-(benzyloxy)ethyl)-6-fluoro-3-phenyl-4H-chromen-4-one

To 1-(5-fluoro-2-hydroxyphenyl)-2-phenylethanone (2.00 g, 8.68 mmol), in dichloromethane (15 ml), HATU (6.60 g, 17.36 mmol), and R-(+)2-benzyloxypropionic acid (1.87 g, 10.42 mmol) were added and stirred for 10 min. Triethylamine (13.0 ml, 93.7 mmol) was added dropwise and stirred at RT for 24 h. The reaction mixture was quenched with water, extracted with dichloromethane, dried over sodium sulphate and concentrated under reduced pressure. The crude product was purified by column chromatography with ethyl acetate:petroleum ether to afford the title compound as a yellow solid (0.634 g, 19%). $^1$H-NMR (8 ppm, CDCl$_3$, 400 MHz): 7.87 (dd, J=8.2, 3.1 Hz, 1H), 7.59 (dd, J=9.1, 4.1 Hz, 1H), 7.45-7.37 (m, 4H), 7.25-7.15 (m, 7H), 4.53 (q, J=6.5 Hz, 1H), 4.43 (d, J=11.8 Hz, 1H), 4.33 (d, J=11.7 Hz, 1H), 1.56 (d, J=6.5 Hz, 3H). Mass: 375.0 (M$^+$).

Step 2: (R)-6-fluoro-2-(1-hydroxyethyl)-3-phenyl-4H-chromen-4-one

To (R)-2-(1-(benzyloxy)ethyl)-6-fluoro-3-phenyl-4H-chromen-4-one (0.63 g, 1.68 mmol) in dichloromethane (6 ml) cooled to 0° C., aluminium chloride (0.330 g, 2.52 mmol) was added portion wise and stirred at RT for 6 h. The reaction mixture was quenched with 2N HCl solution, extracted with dichloromethane, dried over sodium sulphate and concentrated under reduced pressure. The crude product was purified by column chromatography with ethyl acetate:petroleum ether to afford the title compound as yellow solid (0.348 g, 73%). $^1$H-NMR (δ ppm, CDCl$_3$, 400 MHz): 7.83 (m, 1H), 7.76 (m, 2H), 7.46 (m, 3H), 7.30 (m, 2H), 5.60 (d, J=4.9 Hz, 1H), 4.53 (m, 1H), 1.38 (d, J=6.5 Hz, 3H). Mass: 285.2 (M$^+$+1). Purity: 86.82%. [α]$^{25}_D$ −1.18 (c=1, CHCl$_3$). Enantiomeric excess: 97.8%, enriched in the late eluting isomer (retention time: 11.39 min.) as determined by HPLC on a chiralpak AD-H column.

Example 4

(R)-2-(1-hydroxyethyl)-3-phenyl-4H-chromen-4-one

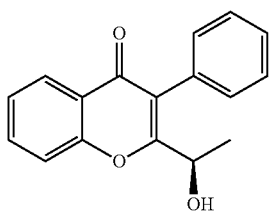 [SMILES: C[C@@H](O)c1oc2ccccc2c(=O)c1-c1ccccc1]

Step 1: (R)-2-(1-(benzyloxy)ethyl)-3-phenyl-4H-chromen-4-one

The title compound was obtained as a yellow solid (1.50 g, 37%) by following the procedure described for Step 1 of Example 3 from 1-(2-hydroxyphenyl)-2-phenylethanone (2.40 g, 11.30 mmol), dichloromethane (30 ml), HATU (8.60 g, 22.60 mmol), R-(+)2-benzyloxypropionic acid (2.44 g, 13.56 mmol) and triethylamine (17.0 ml, 122.11 mmol) which was used as such in next step.

Step 2: (R)-2-(1-hydroxyethyl)-3-phenyl-4H-chromen-4-one

The title compound was obtained as a yellow solid (0.650 g, 58%) by following the procedure described for Step 2 of Example 3 from (R)-2-(1-(benzyloxy)ethyl)-3-phenyl-4H-chromen-4-one (1.50 g, 4.20 mmol) in dichloromethane (15 ml) cooled to 0° C. and aluminium chloride (0.843 g, 6.30 mmol). $^1$H-NMR (δ ppm, CDCl$_3$, 400 MHz): 8.24 (dd, J=7.9, 1.5 Hz, 1H), 7.72 (m, 1H), 7.54 (d, J=8.0 Hz, 1H), 7.46-7.37 (m, 4H), 7.29 (m, 2H), 4.79 (q, J=6.6 Hz, 1H), 1.55 (d, J=6.6 Hz, 3H). Mass: 267.0 (M$^+$). Purity: 98.28%. [α]$^{25}_D$ 6.53 (c=1, CHCl$_3$). Enantiomeric excess: 92.2%, enriched in the late eluting isomer (retention time: 10.38 min.) as determined by HPLC on a chiralpak AD-H column.

Example 5

(R)-3-(3-fluorophenyl)-2-(1-hydroxypropyl)-4H-chromen-4-one

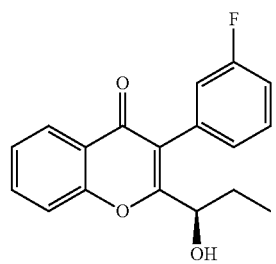 [SMILES: CC[C@@H](O)c1oc2ccccc2c(=O)c1-c1cccc(F)c1]

Step 1: (R)-2-(1-(benzyloxy)propyl)-3-(3-fluorophenyl)-4H-chromen-4-one

The title compound was obtained as a yellow solid (1.65 g, 45%) by following the procedure described for Step 1 of Example 3 from 2-(3-fluorophenyl)-1-(2-hydroxyphenyl)ethanone (2.15 g, 9.36 mmol), dichloromethane (20 ml). HATU (4.27 g, 11.23 mmol), R-(+)2-benzyloxybutyric acid (2.00 g, 10.29 mmol) and triethylamine (14.0 ml, 101.1 mmol). $^1$H-NMR (δ ppm, CDCl$_3$, 400 MHz): 8.24 (dd, J=7.9, 1.5 Hz, 1H), 7.74 (dt, J=7.1, 1.7 Hz, 1H), 7.58 (dd, J=8.3, 0.4 Hz, 1H), 7.44-7.06 (m, 10H), 4.51 (d, J=7.8 Hz, 1H), 4.34 (d, J=7.8 Hz, 1H), 4.25 (dd, J=7.8, 6.2 Hz, 1H), 2.17-1.90 (m, 2H), 0.95 (t, J=7.5 Hz, 3H). Mass: 389.0 (M$^+$).

Step 2: (R)-3-(3-fluorophenyl)-2-(1-hydroxypropyl)-4H-chromen-4-one

The title compound was obtained as a yellow solid (0.552 g, 48%) by following the procedure described for Step 2 of Example 3 from (R)-2-(1-(benzyloxy)propyl)-3-(3-fluorophenyl)-4H-chromen-4-one (1.50 g, 3.86 mmol) in dichloromethane (15 ml) cooled to 0° C. and aluminium chloride (1.00 g, 7.72 mmol). $^1$H-NMR (δ ppm, CDCl$_3$, 400 MHz): 8.24 (dd, J=8.0, 1.6 Hz, 1H), 7.72 (m, 1H), 7.52 (dd, J=8.4, 0.5 Hz, 1H), 7.44 (m, 2H), 7.12-7.01 (m, 3H), 4.49 (t, J=7.0 Hz, 1H), 1.94 (m, 2H), 0.93 (t, J=7.5 Hz, 3H). Mass: (299.0 (M$^+$). Purity: 96.93%. [α]$^{25}_D$ −14.73 (c=1, CHCl$_3$). Enantiomeric excess: 85.92%, enriched in the fast eluting isomer (retention time: 8.57 min.) as determined by HPLC on a chiralpak AS-3R column.

Example 6

(R)-3-(3-fluorophenyl)-2-(1-hydroxyethyl)-4H-chromen-4-one

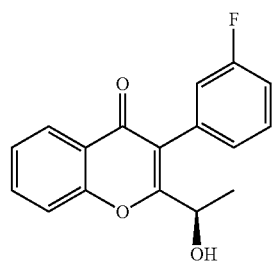 [SMILES: C[C@@H](O)c1oc2ccccc2c(=O)c1-c1cccc(F)c1]

Step-1: (R)-2-(1-(benzyloxy)ethyl)-3-(3-fluorophenyl)-4H-chromen-4-one

To 2-(3-fluorophenyl)-1-(2-hydroxyphenyl)ethanone (10.0 g, 43.43 mmol) in dichloromethane (75 ml), HATU (33.0 g, 86.86 mmol) and R-(+)2-benzyloxypropionic acid (9.39 g, 52.12 mmol) were added and stirred for 10 min. Triethylamine (65.4 ml, 0.469 mol) was added dropwise and stirred at RT for 24 h. The reaction mixture was quenched with water, extracted with dichloromethane, dried over sodium sulphate and concentrated under reduced pressure. The crude product was purified by column chromatography with ethyl acetate:petroleum ether to afford the title compound as a off-white solid (9.0 g, 55%). $^1$H-NMR (δ ppm, CDCl$_3$, 400 MHz): 8.23 (dd, J=7.9, 1.2 Hz, 1H), 7.74-7.70 (m, 1H), 7.58 (d, J=8.3 Hz, 1H), 7.43 (t, J=7.2 Hz, 1H), 7.37 (q, J=7.2 Hz, 1H), 7.29-7.15 (m, 5H), 7.09 (dt, J=8.6, 1.7 Hz, 1H), 7.00-6.90 (m, 2H), 4.51-4.35 (m, 3H), 1.57 (d, J=6.4 Hz, 3H).

Step 2: (R)-3-(3-fluorophenyl)-2-(1-hydroxyethyl)-4H-chromen-4-one

To (R)-2-(1-(benzyloxy)ethyl)-3-(3-fluorophenyl)-4H-chromen-4-one (5.0 g, 13.35 mmol) in dichloromethane (50 ml) cooled to −78° C., boron tribromide (IM in dichloromethane, 36.5 ml, 0.145 mmol) was added dropwise and stirred for 1 h. The reaction mixture was quenched with 2N HCl solution, extracted with dichloromethane, dried over sodium sulphate and concentrated under reduced pressure. The crude product was purified by column chromatography with ethyl acetate:petroleum ether to afford (R)-3-(3-fluorophenyl)-2-(1-hydroxyethyl)-4H-chromen-4-one as an off-white solid (3.05 g, 80%). $^1$H-NMR (δ ppm, CDCl$_3$, 400 MHz): 8.24 (dd, J=7.9, 1.5 Hz, 1H), 7.73 (m, 1H), 7.54 (d, J=8.1 Hz, 1H), 7.44 (m, 2H), 7.13-7.01 (m, 3H), 4.71 (q, J=6.6 Hz, 1H), 1.56 (d, J=6.5 Hz, 3H). Mass: 284.9 (M$^+$). Purity: 99.73%. [α]$^{25}_D$ −0.605 (c=1, CHCl$_3$). Enantiomeric excess: 95.2%, enriched in the late eluting isomer (retention time: 10.19 min.) as determined by HPLC on a chiralpak AD-H column.

Example 7

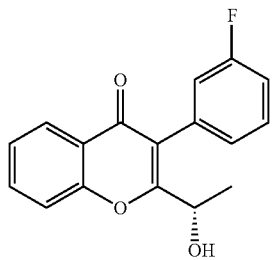 [SMILES: C[C@H](O)c1oc2ccccc2c(=O)c1-c1cccc(F)c1]

Step-1: (S)-1-(3-(3-fluorophenyl)-4-oxo-4H-chromen-2-yl)ethyl 4-chlorobenzoate To a solution of Example 6 (2.00 g, 7.03 mmol) in THF (20 ml), 4-chlorobenzoic acid (1.10 g, 2.15 mmol) and triphenylphosphine (2.70 g, 10.55 mmol) were added and heated to 45° C. followed by and diisopropylazodicarboxylate (2.0 ml, 10.55 mmol). The mixture was refluxed for h, concentrated and the residue was purified by column chromatography with ethyl acetate:petroleum ether to afford the title compound as off-white solid (2.35 g, 79%) which was used without purification in the next step.

Step-2: (S)-3-(3-fluorophenyl)-2-(1-hydroxyethyl)-4H-chromen-4-one

To (R)-11-(3-(3-fluorophenyl)-4-oxo-4H-chromen-2-yl) ethyl 4-chlorobenzoate (2.35 g, 5.55 mmol) in methanol (20 ml), potassium carbonate (0.384 g, 2.77 mmol) was added at 0° C. After 30 min. the methanol was concentrated, quenched with 2N HCl and extracted with ethyl acetate. The organic layer was dried over sodium sulphate and concentrated under reduced pressure. The crude product was purified by column chromatography with ethyl acetate:petroleum ether to afford(S)-3-(3-fluorophenyl)-2-(1-hydroxyethyl)-4H-chromen-4-one as pale yellow solid (1.15 g, 73%). Enantiomeric excess: 95.2%, enriched in the fast eluting isomer (retention time: 8.75 min.) as determined by HPLC on a chiralpak AD-H column.

In order to fully understand and demonstrate the various embodiment of the invention, provided herein below are certain examples in detail as an illustration to enable the utility and/or performance of the present invention.

Illustration 1

(R)-2-(1-(4-amino-3-(3-fluoro-4-morpholinophenyl)-1H-pyrazolo[3,4-d]py-rimidin-1-yl)ethyl)-5-fluoro-3-(3-fluorophenyl)-4H-chromen-4-one This example is also described in Example 59 of WO 2012/151525. To a solution of 3-(3-fluoro-4-morpholinophenyl)-1H-pyrazolo[3,4-d]pyrimidin-4-amine (0.080 g, 0.254 mmol) in THF (2 ml), tris(4-methoxyphenyl)phosphine (0.134 g, 0.381 mmol) and diisopropylazodicarboxylate (0.07 ml, 0.381 mmol) is added and stirred at room temperature (RT) for 10 minutes. To this mixture (−)-5-fluoro-3-(3-fluorophenyl)-2-(l-hydroxyethyl)-4H-chromen-4-one (0.077 g, 0.254 mmol) is added and stirred for 12 h. The reaction mixture is diluted with water and extracted with ethyl acetate. The organic layer is dried over sodium sulphate and concentrated under reduced pressure. The crude product is purified by column chromatography with methanol:dichloromethane to afford the title compound as an off-white solid. MP: 242-245° C. Enantiomeric excess: 96.21% Mass: 599.1 (M$^+$+1).

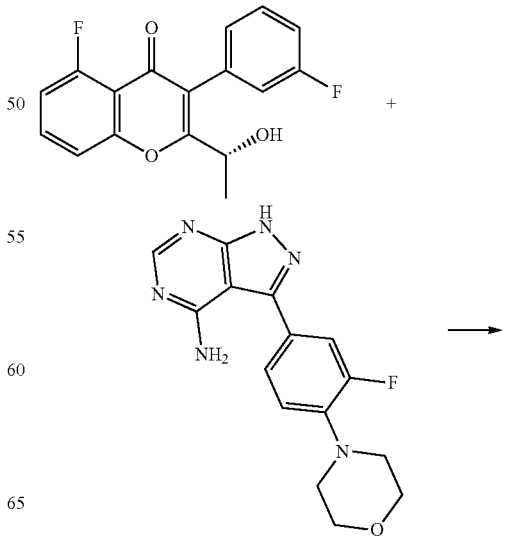

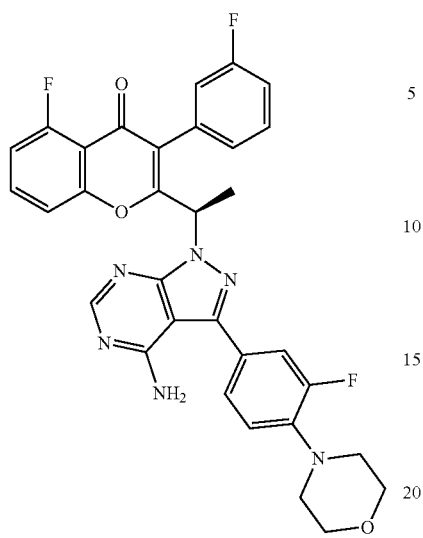

Illustration 2

(+)-2-(1-(9H-purin-6-ylamino)ethyl)-5-fluoro-3-(3-fluorophenyl)-4H-chromen-4-one This example is also described in Example 68 of WO 2012/151525. The title compound is obtained as an off-white solid using a procedure that is similar to the one described for illustration 1 from tert-butyl 9-trityl-9H-purin-6-ylcarbamate (0.235 g, 0.494 mmol), (−)-5-fluoro-3-(3-fluorophenyl)-2-(1-hydroxyethyl)-4H-chromen-4-one (0.150 g, 0.494 mmol), triphenylphosphine (0.194 g, 0.741 mmol), THF (8 ml) and diisopropylazodicarboxylate (0.15 ml, 0.749 mmol), followed by the cleavage of the intermediate with trifluoroacetic acid (1.8 ml) and dichloromethane (5 ml). MP: 194-197° C. Enantiomeric excess: 99.62%. $[\alpha]^{25}_D$ 142.00 (c=1, CHCl$_3$). Mass: 420.1 (M$^+$+1).

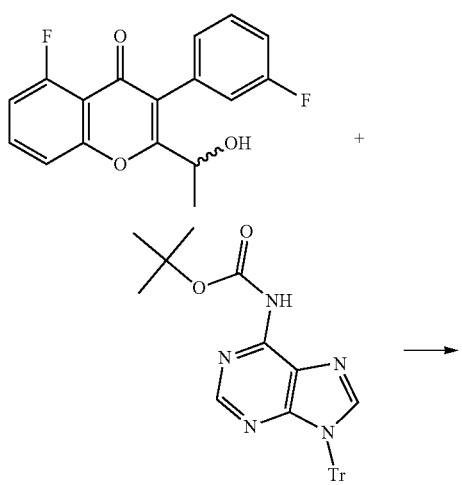

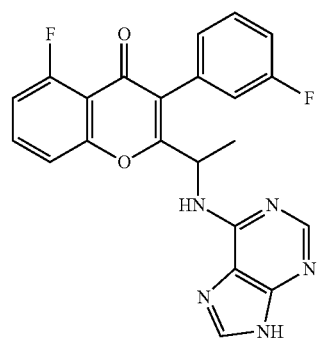

Illustration 3

(+) 2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one This example is also described in Example 114 of WO 2012/151525. The title compound is obtained as off-white solid using a procedure that is similar to the one described for Illustration 1 from 3-(4-isopropoxy-3-methylphenyl)-1H-pyrazolo[3,4-d]pyrimidin-4-amine (0.150 g, 0.529 mmol), (−)-5-fluoro-3-(3-fluorophenyl)-2-(1-hydroxyethyl)-4H-chromen-4-one (0.145 g, 0.481 mmol), tris-4-methoxytriphenylphosphine (0.254 g, 0.721 mmol), THF (3 ml) and diisopropylazodicarboxylate (0.14 ml, 0.721 mmol). MP: 217-220° C. $^1$H-NMR (δ. ppm, CDCl$_3$, 400 MHz): δ 8.22 (s, 1H), 7.61 (dt, J=8.4, 5.4 Hz, 1H), 7.43 (m, 2H), 7.29 (m, 2H), 7.05-6.97 (m, 4H), 6.92 (d, J=9.4 Hz, 1H), 6.07 (q, J=7.1 Hz, 1H), 5.42 (s, 2H), 4.63 (quintet, J=6.0 Hz, 1H), 2.28 (s, 3H), 1.97 (d, J=7.1 Hz, 3H), 1.39 (d, J=6.0 Hz, 6H). Enantiomeric excess: 100% as determined by HPLC on a chiralpak AD-H column, enriched in the fast eluting isomer (retention time=9.36 min) $[\alpha]^{25}_D$ 176.04 (c=1, CHCl$_3$).

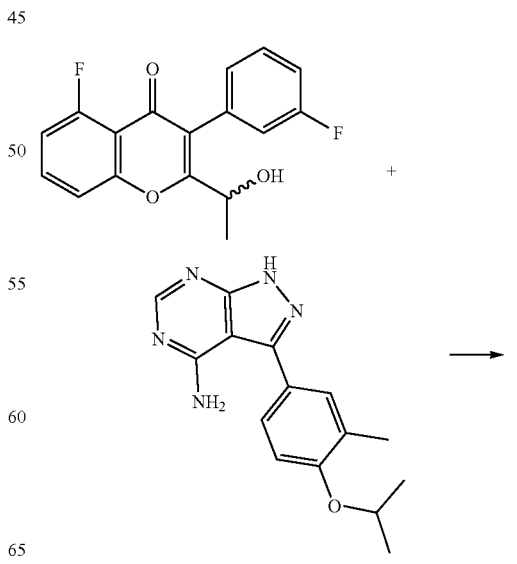

-continued

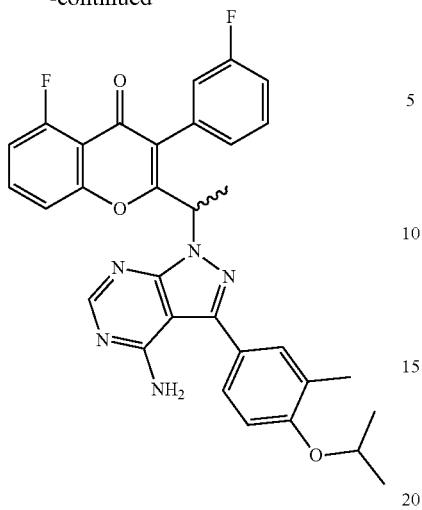

Illustration 4

(−) 2-(1-(4-amino-3-(4-isopropoxy-3-methylphenyl)-1H-pyrazolo[3,4-d]pyrimi-din-1-yl)ethyl)-5-fluoro-3-(3-fluorophenyl)-4H-chromen-4-one This example is also described in Example 115 of WO 2012/151525. The title compound is obtained as an off-white solid using a procedure that is similar to the one described for Illustration 1 from 3-(4-isopropoxy-3-methylphenyl)-1H-pyrazolo[3,4-d]pyrimidin-4-amine (0.128 g, 0.453 mmol), (+)-5-fluoro-3-(3-fluorophenyl)-2-(1-hydroxyethyl)-4H-chromen-4-one (0.125 g, 0.412 mmol), tris-4-methoxytriphenylphosphine (0.217 g, 0.618 mmol), THF (3 ml) and diisopropylazodicarboxylate (0.12 ml, 0.618 mmol). MP: 221-224° C. $^1$H-NMR (δ ppm, CDCl$_3$, 400 MHz): δ 8.22 (s, 1H), 7.61 (dt, J=8.4, 5.5 Hz, 1H), 7.43 (m, 2H), 7.29 (m, 2H), 7.05-6.95 (m, 4H), 6.92 (d, J-=9.5 Hz, 1H), 6.05 (q, J=7.1 Hz, 1H), 5.40 (s, 2H), 4.62 (quintet, J=6.0 Hz, 1H), 2.28 (s, 3H), 1.99 (d, J=7.2 Hz, 3H), 1.39 (d. J=6.0 Hz, 6H). Enantiomeric excess: 99.6% as determined by HPLC on a chiralpak AD-H column, enriched in the late eluting isomer (retention time=11.43 min) $[α]^{35}_D$ − 183.59 (c=1, CHCl$_3$).

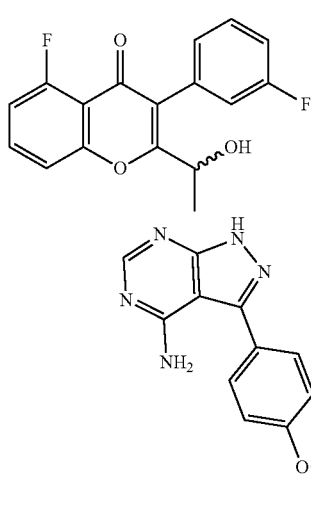

-continued

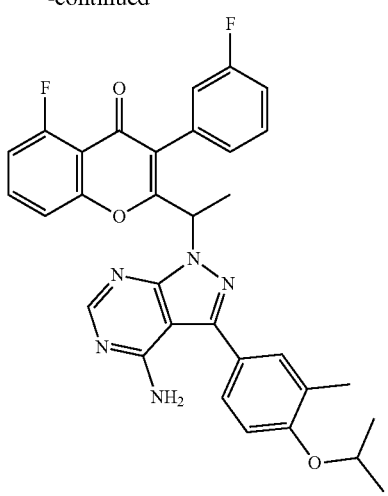

Illustration 5

(S)/(R)-2-(1-aminoethyl)-5-fluoro-3-(3-fluorophenyl)-4H-chromen-4-one

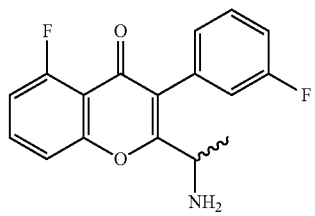 [SMILES: CC(N)c1oc2cccc(F)c2c(=O)c1-c1cccc(F)c1]

This example is also described in Intermediate 141-143 of WO 2012/151525.

Step-1

(S)/(R)-1-(5-fluoro-3-(3-fluorophenyl)-4-oxo-4H-chromen-2-yl)ethyl methanesulfonate: To a cooled solution of (+)-5-fluoro-3-(3-fluorophenyl)-2-(1-hydroxyethyl)-4H-chromen-4-one (0.800 g, 2.63 mmol) in dichloromethane (16 ml) and triethylamine (1.10 ml, 7.91 mmol), methanesulfonyl chloride (0.400 ml, 5.27 mmol) is added stirred at room temperature for 2 h. The reaction mass is quenched with water, extracted with dichloromethane, dried over sodium sulphate and concentrated to afford the title compound as brown solid which is used as such in next step.

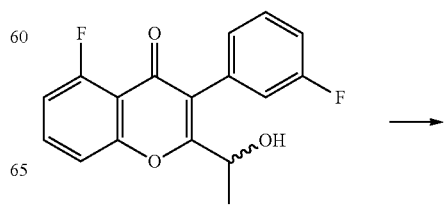

-continued

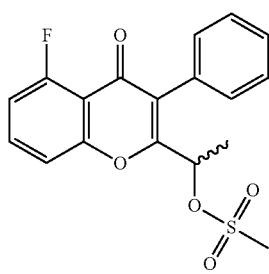

Step-2

(S)/(R)-2-(1-azidoethyl)-5-fluoro-3-(3-fluorophenyl)-4H-chromen-4-one: To a solution of (S)/(R)-1-(5-fluoro-3-(3-fluorophenyl)-4-oxo-4H-chromen-2-yl)ethyl methane sulfonate (0.900 g, 2.36 mmol) in DMF (18 ml), sodium azide (0.306 g, 4.72 mmol) is added and heated to 60° C. After 2 h, the reaction mass is quenched with water, extracted with dichloromethane, dried over sodium sulphate and concentrated. The crude product is column chromatographed with ethyl acetate:petroleum ether to afford the title compound as a brown liquid which is used as such in next step.

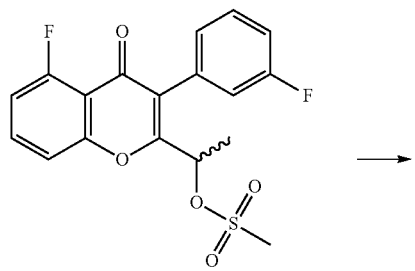

Step-3

(S)/(R)-2-(1-aminoethyl)-5-fluoro-3-(3-fluorophenyl)-4H-chromen-4-one: To a solution of (S)/(R)-2-(1-azido-ethyl)-5-fluoro-3-(3-fluorophenyl)-4H-chromen-4-one (0.600 g, 1.82 mmol) in THF (2.4 ml) and water (1.2 ml), triphenylphosphine (0.455 g, 1.73 mmol) is added and stirred at room temperature for 14 h. The reaction mass is quenched with water, extracted with ethyl acetate, dried over sodium sulphate and concentrated. The crude product is column chromatographed with methanol:dichloromethane to afford the title compound as a brown liquid.

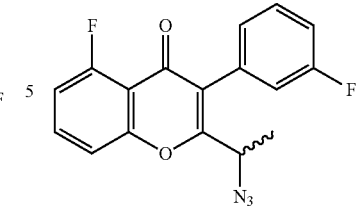

Illustration 6

(S)/(R)-5-fluoro-2-(1-(2-fluoro-9H-purin-6-ylamino)ethyl)-3-(3-fluorophenyl-1)-4H-chromen-4-one This example is also described in Example 136 of WO 2012/151525. To a solution of (S)/(R)-2-(1-aminoethyl)-5-fluoro-3-(3-fluorophenyl)-4H-chromen-4-one (0.22 g, 0.730 mmol), tert-butanol (1.5 ml) N,N-diisopropylethylamine (0.25 ml, 1.46 mmol) and 6-chloro-2-fluoro-9H-purine (0.102 g, 0.663 mmol) are added and heated to reflux for 248 h. The reaction mixture is concentrated, quenched with water, extracted with ethyl acetate, dried with sodium sulphate and concentrated. The crude product is purified by column chromatography with methanol:ethyl acetate to afford the title compound as a brown solid. MP: 183-186° C. Mass: 437.9 (M$^+$). Enantiomeric excess: 33% as determined by HPLC on a chiralpak AD-II column, enriched in the fast eluting isomer (retention time=7.21 min).

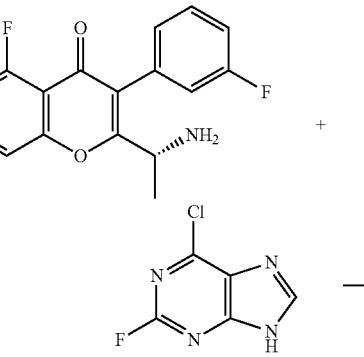

Illustration 7

(S)-2-(1-(9H-purin-6-ylamino) ethyl)-6-bromo-3-phenyl-4H-chromen-4-one

This example is also described in Example 24 of WO 2011/055215. To a solution of (S)-2-(1-aminoethyl)-6-bromo-3-phenyl-4H-chromen-4-one (0.20 g, 0.581 mmoles) in tert-butanol (6 ml), N,N-diisopropylethyl amine (0.2 ml, 1.162 mmoles) and 6-bromopurine (0.087 g, 0.435 mmoles) are added and refluxed for 24 h. The reaction mixture is concentrated, diluted with water, extracted with ethyl acetate. The organic layer is dried over sodium sulphate and concentrated under reduced pressure. The crude product is purified by column chromatography with methanol:ethyl acetate to afford the title compound as yellow solid. MP: 151-154° C. $^1$H-NMR (δ ppm. DMSO-D$_6$, 400 MHz): δ 12.94 (s, 1H), 8.09 (br s, 3H), 7.94 (d, J=7.9 Hz, 1H), 7.59 (d, J=8.7 Hz, 1H), 7.42 (m, 6H), 5.22 (br t, 1H), 1.82 (d, J=6.4 Hz, 3H). Mass: 463.99 (M+1).

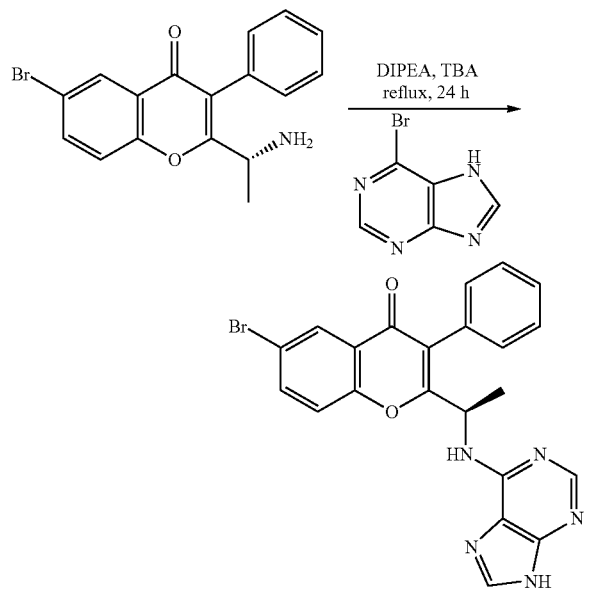

Illustration 8

(R)-2-(1-(9H-purin-6-ylamino) ethyl)-3-(3-fluoro-phenyl)-4H-chromen-4-one

This example is also described in Example 56 of WO 2011/055215. To a solution of (R)-2-(1-Amino-ethyl)-3-(3-fluoro-phenyl)-chromen-4-one (0.41 g, 1.52 mmoles) in tert-butanol (7 ml), N,N-diisopropylethylamine (0.53 ml, 3.04 mmoles) and 6-bromopurine (0.242 g, 1.21 mmoles) are added and refluxed for 24 h. The reaction mixture is concentrated, diluted with water, and extracted with ethyl acetate. The organic layer is dried over sodium sulphate and concentrated under reduced pressure. The crude product is purified by column chromatography with methanol:ethyl acetate to afford the title compound as an off-white solid. MP: 274-276° C. $^1$H-NMR (δ ppm, DMSO-D$_6$, 400 MHz): δ 12.96 (s, 1H), 8.14-8.01 (m, 4H), 8.11 (s, 1H), 7.81 (dt, J=8.5, 1.5 Hz, 1H), 7.60 (d, J=8.4 Hz, 1H), 7.49 (m, 2H), 7.25-7.19 (m, 3H), 5.18 (br m, 1H), 1.56 (d, J=7.0 Hz, 3H). Mass: 402.04 (M$^+$+1).

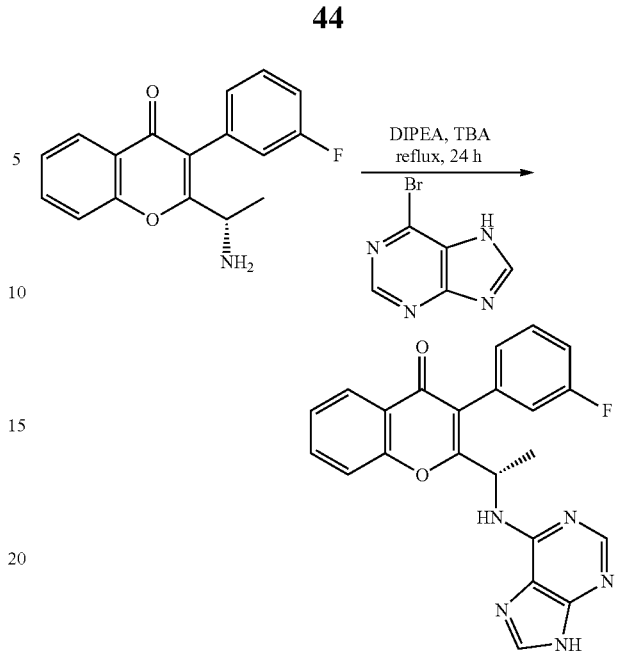

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent, or patent application was specifically and individually indicated to be incorporated herein by reference.

The invention claimed is:

1. A process for preparing a PI3K inhibitor of formula (I)

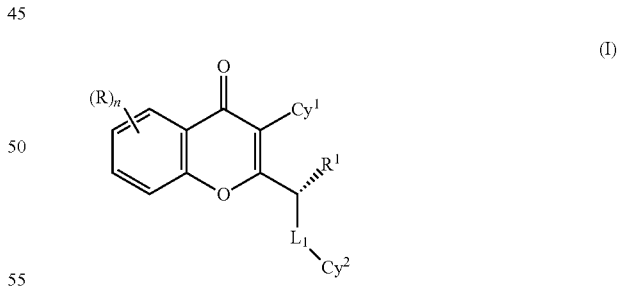

or a tautomer thereof, N-oxide thereof, pharmaceutically acceptable ester thereof, prodrug thereof, or pharmaceutically acceptable salt thereof, wherein each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^x$R$^y$, —N(R$^x$)SOR$^x$, —N(R$^x$)SO$_2$R$^y$, —NR$^x$C(O)OR$^y$, —NR$^x$C(O)R$^y$, —NR$^x$C(S)R$^y$, —NR$^x$C(S)NR$^x$R$^y$, —SONR$^x$R$^y$, —SO$_2$NR$^x$R$^y$, —OR$^x$, —OR$^x$C(O)NR$^x$R$^y$, —OR$^x$C(O)OR$^x$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO$_2$R$^x$, and —ONO$_2$, wherein each occurrence of R$^x$, R$^y$ and R$^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of R$^x$ and R$^y$, when bound to a common atom, are joined to form a substituted or unsubstituted, saturated or unsaturated 3-14 membered ring, which may optionally include heteroatoms which may be the same or different and are selected from O, NR$^z$ or S, or (ii) any two of R$^x$ and R$^y$, when bound to a common atom, are joined to form an oxo (=O), thio (=S) or imino (=NR$^f$) (wherein R$^f$ is hydrogen or substituted or unsubstituted alkyl);

R$^1$ is substituted or unsubstituted C$_{1-6}$ alkyl;

Cy$^1$ is a monocyclic or bicyclic group selected from substituted or unsubstituted cycloalkyl, substituted or unsubstituted heterocyclic group, substituted or unsubstituted aryl and substituted or unsubstituted heteroaryl;

n is an integer selected from 0, 1, 2, 3 or 4;

Cy$^2$ is selected from a substituted or unsubstituted heterocyclic group, substituted or unsubstituted aryl and substituted or unsubstituted heteroaryl;

L$_1$ is absent;

each occurrence of R$^a$ and R$^b$ may be the same or different and are independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, or (C$_{1-6}$)alkoxy) and —OR$^c$ (wherein R$^c$ is substituted or unsubstituted (C$_{1-6}$)alkyl) or when R$^a$ and R$^b$ are directly bound to a common atom, they may be joined to form an oxo group (=O) or form a substituted or unsubstituted, saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted (C$_{1-6}$)alkyl) or S;

Y is selected from O, S, and NR$^a$; and q is 0, 1 or 2, the process comprising (a) treating a compound of formula (IA)

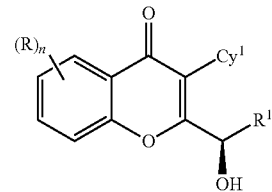

IA where variables R, n, Cy$^1$, and R$^1$ are as defined above, with Cy$^2$-H to give the desired compound of formula (I) or a tautomer thereof, N-oxide thereof, pharmaceutically acceptable ester thereof, prodrug thereof, or pharmaceutically acceptable salt thereof; and (b) optionally converting the compound of formula (I) to a salt of the compound.

2. A process for preparing a PI3K inhibitor of formula (I)

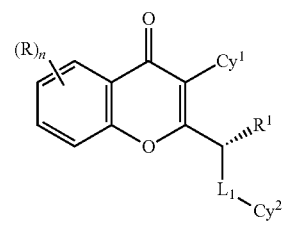

(I)

or a tautomer thereof, N-oxide thereof, pharmaceutically acceptable ester thereof, prodrug thereof, or pharmaceutically acceptable salt thereof, wherein each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^x$R$^y$, —N(R$^x$)SOR$^x$, —N(R$^x$)SO$_2$R$^y$, —NR$^x$C(O)OR$^y$, —NR$^x$C(O)R$^y$, —NR$^x$C(S)R$^y$, —NR$^x$C(S)NR$^x$R$^y$, —SONR$^x$R$^y$, —SO$_2$NR$^x$R$^y$, —OR$^x$, —OR$^x$C(O)NR$^x$R$^y$, —OR$^x$C(O)OR$^x$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO$_2$R$^x$, and —ONO$_2$, wherein each occurrence of R$^x$, R$^y$ and R$^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of $R^x$ and $R^y$, when bound to a common atom, are joined to form a substituted or unsubstituted, saturated or unsaturated 3-14 membered ring, which may optionally include heteroatoms which may be the same or different and are selected from O, $NR^z$ or S, or (ii) any two of $R^x$ and $R^y$, when bound to a common atom, are joined to form an oxo (=O), thio (=S) or imino (=$NR^f$) (wherein $R^f$ is hydrogen or substituted or unsubstituted alkyl);

$R^1$ is substituted or unsubstituted $C_{1-6}$ alkyl;

$Cy^1$ is a monocyclic or bicyclic group selected from substituted or unsubstituted cycloalkyl, substituted or unsubstituted heterocyclic group, substituted or unsubstituted aryl and substituted or unsubstituted heteroaryl;

n is an integer selected from 0, 1, 2, 3 or 4;

$Cy^2$ is selected from a substituted or unsubstituted heterocyclic group, substituted or unsubstituted aryl and substituted or unsubstituted heteroaryl;

$L_1$ is absent;

each occurrence of $R^a$ and $R^b$ may be the same or different and are independently selected from hydrogen, halogen, hydroxy, cyano, substituted or unsubstituted ($C_{1-6}$)alkyl, —$NR^cR^d$ (wherein $R^c$ and $R^d$ are independently hydrogen, halogen, hydroxy, cyano, substituted or unsubstituted ($C_{1-6}$)alkyl, or ($C_{1-6}$)alkoxy) and —$OR^c$ (wherein $R^c$ is substituted or unsubstituted ($C_{1-6}$)alkyl) or when $R^a$ and $R^b$ are directly bound to a common atom, they may be joined to form an oxo group (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, $NR^d$ (wherein $R^d$ is hydrogen or substituted or unsubstituted ($C_{1-6}$)alkyl) or S;

Y is selected from O, S, and $NR^a$; and q is 0, 1 or 2, the process comprising (a) treating a compound of formula (IA)

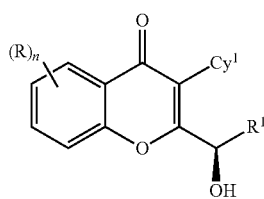

IA where variables R, n, $Cy^1$, and $R^1$ are as defined above, with mesyl halide in the presence of a base to give a compound of formula (8a)

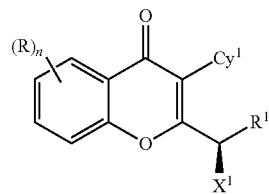

8a wherein $X^1$ is —O-Mesyl; and (b) reacting the compound of formula (8a) with $Cy^2$-H in the presence of a base to give the desired compound of formula (I) or a tautomer thereof, N-oxide thereof, pharmaceutically acceptable ester thereof, prodrug thereof, or pharmaceutically acceptable salt thereof; and (c) optionally, converting the compound of formula (I) to a salt of the compound.

3. A process for preparing a PI3K inhibitor of formula (III)

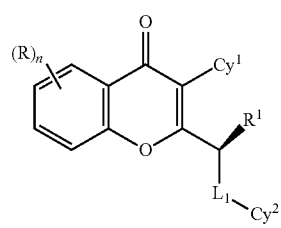

(II)

or a tautomer thereof, N-oxide thereof, pharmaceutically acceptable ester thereof, prodrug thereof, or pharmaceutically acceptable salt thereof, wherein each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^x$, —$C(O)R^x$, —$C(S)R^x$, —$C(O)NR^xR^y$, —$C(O)ONR^xR^y$, —$NR^xR^y$, —$NR^xCONR^xR^y$, —$N(R^x)SOR^x$, —$N(R^x)SO_2R^y$, —$NR^xC(O)OR^y$, —$NR^xC(O)R^y$, —$NR^xC(S)R^y$, —$NR^xC(S)NR^xR^y$, —$SONR^xR^y$, —$SO_2NR^xR^y$, —$OR^x$, —$OR^xC(O)NR^xR^y$, —$OR^xC(O)OR^x$, —$OC(O)R^x$, —$OC(O)NR^xR^y$, —$R^xNR^yC(O)R^z$, —$R^xOR^y$, —$R^xC(O)OR^y$, —$R^xC(O)NR^xR^y$, —$R^xC(O)R^y$, —$R^xOC(O)R^y$, —$SR^x$, —$SOR^x$, —$SO_2R^x$, and —$ONO_2$, wherein each occurrence of $R^x$, $R^y$ and $R^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of $R^x$ and $R^y$, when bound to a common atom, are joined to form a substituted or unsubstituted, saturated or unsaturated 3-14 membered ring, which may optionally include heteroatoms which may be the same or different and are selected from O, $NR^z$ or S, or (ii) any two of $R^x$ and $R^y$, when bound to a common atom, are joined to form an oxo (=O), thio (=S) or imino (=$NR^f$) (wherein $R^f$ is hydrogen or substituted or unsubstituted alkyl);

$R^1$ is substituted or unsubstituted $C_{1-6}$ alkyl;

$Cy^1$ is a monocyclic or bicyclic group selected from substituted or unsubstituted cycloalkyl, substituted or unsubstituted heterocyclic group, substituted or unsubstituted aryl and substituted or unsubstituted heteroaryl;

n is an integer selected from 0, 1, 2, 3 or 4;

$Cy^t$ is selected from a substituted or unsubstituted heterocyclic group, substituted or unsubstituted aryl and substituted or unsubstituted heteroaryl;

$L_1$ is absent;

each occurrence of $R^a$ and $R^b$ may be the same or different and are independently selected from hydrogen, halogen, hydroxy, cyano, substituted or unsubstituted $(C_{1-6})$alkyl, —$NR^cR^d$ (wherein $R^c$ and $R^d$ are independently hydrogen, halogen, hydroxy, cyano, substituted or unsubstituted $(C_{1-6})$alkyl, or $(C_{1-6})$alkoxy) and —$OR^c$ (wherein $R^c$ is substituted or unsubstituted $(C_{1-6})$alkyl) or when $R^a$ and $R^b$ are directly bound to a common atom, they may be joined to form an oxo group (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, $NR^d$ (wherein $R^d$ is hydrogen or substituted or unsubstituted $(C_{1-6})$alkyl) or S;

Y is selected from O, S, and $NR^a$; and q is 0, 1 or 2, the process comprising (a) treating a compound of formula (IB)

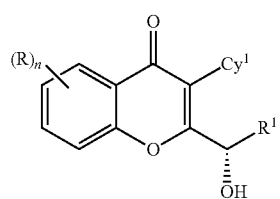

IB where variables R, n, $Cy^1$, and $R^1$ are as defined above, with $Cy^2$-H to give the desired compound of formula (III) or a tautomer thereof, N-oxide thereof, pharmaceutically acceptable ester thereof, prodrug thereof, or pharmaceutically acceptable salt thereof; and (b) optionally converting the compound of formula (III) to a salt of the compound.

4. A process for preparing a PI3K inhibitor of formula (III)

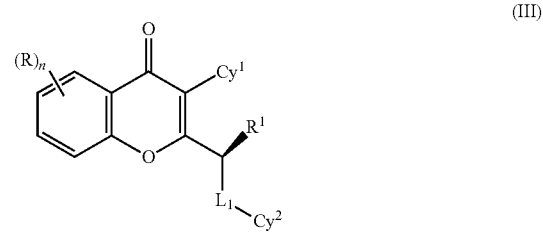

(III)

or a tautomer thereof, N-oxide thereof, pharmaceutically acceptable ester thereof, prodrug thereof, or pharmaceutically acceptable salt thereof, wherein each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^x$, —$C(O)R^x$, —$C(S)R^x$, —$C(O)NR^xR^y$, —$C(O)ONR^xR^y$, —$NR^xR^y$, —$NR^xCONR^xR^y$, —$N(R^x)SOR^x$, —$N(R^x)SO_2R^y$, —$NR^xC(O)OR^y$, —$NR^xC(O)R^y$, —$NR^xC(S)R^y$, —$NR^xC(S)NR^xR^y$, —$SONR^xR^y$, —$SO_2NR^xR^y$, —$OR^x$, —$OR^xC(O)NR^xR^y$, —$OR^xC(O)OR^x$, —$OC(O)R^x$, —$OC(O)NR^xR^y$, —$R^xNR^yC(O)R^z$, —$R^xOR^y$, —$R^xC(O)OR^y$, —$R^xC(O)NR^xR^y$, —$R^xC(O)R^y$, —$R^xOC(O)R^y$, —$SR^x$, —$SOR^x$, —$SO_2R^x$, and —$ONO_2$, wherein each occurrence of $R^x$, $R^y$ and $R^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of $R^x$ and $R^y$, when bound to a common atom, are joined to form a substituted or unsubstituted, saturated or unsaturated 3-14 membered ring, which may optionally include heteroatoms which may be the same or different and are selected from O, $NR^z$ or S, or (ii) any two of $R^x$ and $R^y$, when bound to a common atom, are joined to form an oxo (=O), thio (=S) or imino (=$NR^f$) (wherein $R^f$ is hydrogen or substituted or unsubstituted alkyl);

$R^1$ is substituted or unsubstituted $C_{1-6}$ alkyl;

$Cy^1$ is a monocyclic or bicyclic group selected from substituted or unsubstituted cycloalkyl, substituted or unsubstituted heterocyclic group, substituted or unsubstituted aryl and substituted or unsubstituted heteroaryl;

n is an integer selected from 0, 1, 2, 3 or 4;

Cy² is selected from a substituted or unsubstituted heterocyclic group, substituted or unsubstituted aryl and substituted or unsubstituted heteroaryl;

L₁ is absent;

each occurrence of $R^a$ and $R^b$ may be the same or different and are independently selected from hydrogen, halogen, hydroxy, cyano, substituted or unsubstituted (C₁₋₆)alkyl, —NR$^c$R$^d$ (wherein R$^c$ and R$^d$ are independently hydrogen, halogen, hydroxy, cyano, substituted or unsubstituted (C₁₋₆)alkyl, or (C₁₋₆)alkoxy) and —OR$^c$ (wherein R$^c$ is substituted or unsubstituted (C₁₋₆)alkyl) or when $R^a$ and $R^b$ are directly bound to a common atom, they may be joined to form an oxo group (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, NR$^d$ (wherein R$^d$ is hydrogen or substituted or unsubstituted (C₁₋₆)alkyl) or S;

Y is selected from O, S, and NR$^a$; and q is 0, 1 or 2, the process comprising (a) treating the compound of formula (IB)

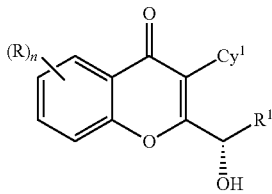

IB where variables R, n, Cy¹, and R¹ are as defined above, with a phosphorus halide or mesyl halide in the presence of a base to give a compound of formula (8b)

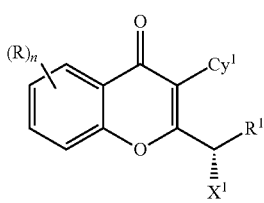

8b wherein X¹ is halogen or —O-Mesyl; and (b) reacting the compound of formula (8b) with Cy²-H in the presence of a base to give the desired compound of formula (III) or a tautomer thereof, N-oxide thereof, pharmaceutically acceptable ester thereof, prodrug thereof, or pharmaceutically acceptable thereof; and (c) optionally, converting the compound of formula (III) to a salt of the compound.

5. A process for preparing a PI3K inhibitor of formula (I)

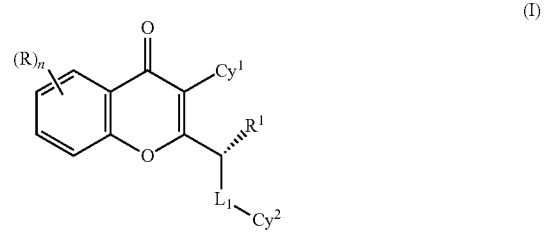

(I)

or a tautomer thereof, N-oxide thereof, pharmaceutically acceptable ester thereof, prodrug thereof, or pharmaceutically acceptable salt thereof, wherein each occurrence of R is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^x$R$^y$, —N(R$^x$)SOR$^x$, —N(R$^x$)SO₂R$^y$, —NR$^x$C(O)OR$^y$, —NR$^x$C(O)R$^y$, —NR$^x$C(S)R$^y$, —NR$^x$C(S)NR$^x$R$^y$, —SONR$^x$R$^y$, —SO₂NR$^x$R$^y$, —OR$^x$, —OR$^x$C(O)NR$^x$R$^y$, —OR$^x$C(O)OR$^x$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO₂R$^x$, and —ONO₂, wherein each occurrence of R$^x$, R$^y$ and R$^z$ is independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, or substituted or unsubstituted amino, or (i) any two of R$^x$ and R$^y$, when bound to a common atom, are joined to form a substituted or unsubstituted, saturated or unsaturated 3-14 membered ring, which may optionally include heteroatoms which may be the same or different and are selected from O, NR$^z$ or S, or (ii) any two of R$^x$ and R$^y$, when bound to a common atom, are joined to form an oxo (=O), thio (=S) or imino (=NR$^f$) (wherein R$^f$ is hydrogen or substituted or unsubstituted alkyl);

R¹ is substituted or unsubstituted C₁₋₆ alkyl;

Cy¹ is a monocyclic or bicyclic group selected from substituted or unsubstituted cycloalkyl, substituted or unsubstituted heterocyclic group, substituted or unsubstituted aryl and substituted or unsubstituted heteroaryl;

n is an integer selected from 0, 1, 2, 3 or 4;

Cy² is selected from a substituted or unsubstituted heterocyclic group, substituted or unsubstituted aryl and substituted or unsubstituted heteroaryl;

L₁ is absent;

each occurrence of $R^a$ and $R^b$ may be the same or different and are independently selected from hydrogen, halogen, hydroxy, cyano, substituted or unsubstituted $(C_{1-6})$alkyl, —$NR^cR^d$ (wherein $R^c$ and $R^d$ are independently hydrogen, halogen, hydroxy, cyano, substituted or unsubstituted $(C_{1-6})$alkyl, or $(C_{1-6})$alkoxy) and —$OR^c$ (wherein $R^c$ is substituted or unsubstituted $(C_{1-6})$alkyl) or when $R^a$ and $R^b$ are directly bound to a common atom, they may be joined to form an oxo group (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, $NR^d$ (wherein $R^d$ is hydrogen or substituted or unsubstituted $(C_{1-6})$alkyl) or S;

Y is selected from O, S, and $NR^a$; and q is 0, 1 or 2, the process comprising
(a) treating a compound of formula (IA)

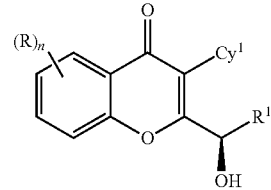

IA where variables R, n, Cy¹, and R¹ are as defined above, with a phosphorus halide in the presence of a base to give an intermediate halide compound; and (b) reacting the intermediate halide compound with Cy²-H in the presence of a base to give the desired compound of formula (I) or a tautomer thereof, N-oxide thereof, pharmaceutically acceptable ester thereof, prodrug thereof, or pharmaceutically acceptable salt thereof; and (c) optionally, converting the compound of formula (I) to a salt of the compound.

* * * * *